(12) United States Patent
Puleo et al.

(10) Patent No.: US 10,518,196 B2
(45) Date of Patent: Dec. 31, 2019

(54) DEVICES FOR SEPARATION OF PARTICULATES, ASSOCIATED METHODS AND SYSTEMS

(71) Applicant: GENERAL ELECTRIC COMPANY, Schenectady, NY (US)

(72) Inventors: Christopher Michael Puleo, Niskayuna, NY (US); Craig Patrick Galligan, Niskayuna, NY (US); Gregory Andrew Grossman, Halfmoon, NY (US); Erik Leeming Kvam, Schenectady, NY (US); Robert Scott Duthie, Schenectady, NY (US); Kenneth Wayne Rigby, Clifton Park, NY (US); Paul Michael Smigelski, Jr., Glenville, NY (US); Victoria Eugenia Cotero, Niskayuna, NY (US); Jason William Castle, Esperance, NY (US); John Donald Burczak, Voorheesville, NY (US); James Edward Rothman, Westhampton, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/209,411

(22) Filed: Jul. 13, 2016

(65) Prior Publication Data

US 2018/0001231 A1 Jan. 4, 2018

Related U.S. Application Data

(63) Continuation-in-part of application No. 14/167,393, filed on Jan. 29, 2014, now abandoned.

(51) Int. Cl.
*B01D 21/00* (2006.01)
*B01D 21/24* (2006.01)
(Continued)

(52) U.S. Cl.
CPC ......... *B01D 21/0087* (2013.01); *B01D 17/02* (2013.01); *B01D 21/0006* (2013.01);
(Continued)

(58) Field of Classification Search
CPC .... B01D 21/0087; B01D 15/08; B01D 15/18; B01D 17/00; B01D 17/06; B01D 17/12;
(Continued)

(56) References Cited

U.S. PATENT DOCUMENTS

| 4,197,847 A | 4/1980 | Djerassi |
| 4,737,268 A * | 4/1988 | Giddings ........... G01N 30/0005 209/12.2 |

(Continued)

FOREIGN PATENT DOCUMENTS

| EP | 0730639 B1 | 4/2003 |
| WO | 2011079217 A1 | 6/2011 |

OTHER PUBLICATIONS

Yue et al., "Miniature Field-Flow Fractionation System for Analysis of Blood Cells", Cunical Chemistry, pp. 1810-1814, vol. 40, Issue 9, 1994.

(Continued)

*Primary Examiner* — Joseph W Drodge
(74) *Attorney, Agent, or Firm* — Eversheds Sutherland (US) LLP

(57) ABSTRACT

A separation device, system and associated method are provided herein for separation of particulates form a base fluid. The separation device comprises a first microchannel comprising a fluid inlet and a mesofluidic collection chamber. The mesofluidic collection chamber has a first side and a second side, wherein the mesofluidic collection chamber is operatively coupled to the first microchannel on the first side, and wherein the mesofluidic collection chamber comprises a first fluid outlet at the second side, such that the fluid inlet, first microchannel, and first fluid outlet are in fluidic communication via the mesofluidic collection chamber.

36 Claims, 17 Drawing Sheets

Specification includes a Sequence Listing.

(51) Int. Cl.

| | | |
|---|---|---|
| G01N 33/49 | (2006.01) | |
| B01L 3/00 | (2006.01) | |
| G01N 1/40 | (2006.01) | |
| C12M 1/12 | (2006.01) | |
| C12M 1/26 | (2006.01) | |
| B01D 17/02 | (2006.01) | |
| B01D 21/02 | (2006.01) | |
| C12M 1/00 | (2006.01) | |
| C02F 1/48 | (2006.01) | |
| C02F 1/44 | (2006.01) | |
| C02F 101/32 | (2006.01) | |

(52) U.S. Cl.
CPC ......... *B01D 21/0042* (2013.01); *B01D 21/10* (2013.01); *B01D 21/2433* (2013.01); *B01D 21/2444* (2013.01); *B01L 3/50273* (2013.01); *B01L 3/502715* (2013.01); *B01L 3/502753* (2013.01); *B01L 3/502761* (2013.01); *C12M 1/123* (2013.01); *C12M 33/22* (2013.01); *C12M 47/04* (2013.01); *G01N 1/4077* (2013.01); *G01N 33/491* (2013.01); *B01D 21/02* (2013.01); *B01D 2221/04* (2013.01); *B01L 2200/0631* (2013.01); *B01L 2200/0647* (2013.01); *B01L 2200/0652* (2013.01); *B01L 2200/0668* (2013.01); *B01L 2300/0681* (2013.01); *B01L 2300/0851* (2013.01); *B01L 2400/043* (2013.01); *B01L 2400/0421* (2013.01); *B01L 2400/0457* (2013.01); *B01L 2400/0469* (2013.01); *C02F 1/444* (2013.01); *C02F 1/48* (2013.01); *C02F 2101/32* (2013.01); *G01N 2001/4083* (2013.01)

(58) Field of Classification Search
CPC .. B01D 21/009; B01D 21/24; B01D 21/2405; B01D 21/2433; B01D 21/28; B01D 21/30; B01D 36/04; B01L 3/50273; B01L 3/502715; B01L 3/502753; B01L 2200/0647; B01L 2400/0457; B01L 3/502; B01L 3/5027; B01L 3/502746; B01L 2200/0652; B01L 2400/04; B01L 2400/0415; B01L 2400/0421; B01L 2400/0424; B01L 2400/043; G01N 1/4077; G01N 33/491; G01N 2001/4083; G01N 1/40; G01N 15/02; G01N 15/0255; G01N 15/0266; G01N 15/0288; G01N 15/05; G01N 15/10; G01N 15/1031; G01N 15/1056; G01N 2015/1081; G01N 2015/1087; G01N 33/4915; C12M 1/12; C12M 1/123
USPC .. 210/143, 223, 243, 321.6, 321.75, 321.84, 210/511, 513, 644, 645, 649, 650, 651, 210/748.01, 748.05, 695, 800, 802; 73/863.21, 863.23; 204/518, 519, 204/542–545, 553, 601, 602, 627, 628; 209/1, 155; 422/527, 533–535
See application file for complete search history.

(56) References Cited

U.S. PATENT DOCUMENTS

| | | | |
|---|---|---|---|
| 5,282,982 A | 2/1994 | Wells | |
| 5,789,148 A | 8/1998 | Van Vlasselaer et al. | |
| 5,961,832 A * | 10/1999 | Shaw | B01D 11/0415 |
| | | | 210/634 |
| 5,971,158 A * | 10/1999 | Yager | B01J 19/0093 |
| | | | 209/155 |
| 6,454,945 B1 * | 9/2002 | Weigl | B01D 11/0492 |
| | | | 204/600 |
| 6,517,234 B1 * | 2/2003 | Kopf-Sill | B01J 19/0093 |
| | | | 366/340 |
| 6,706,519 B1 * | 3/2004 | Kellogg | B01F 13/0064 |
| | | | 422/64 |
| 7,264,608 B2 | 9/2007 | Bischof et al. | |
| 8,097,153 B2 | 1/2012 | Leonard et al. | |
| 8,157,774 B1 | 4/2012 | Altobelli | |
| 8,241,592 B2 | 8/2012 | Duffy et al. | |
| 8,263,359 B2 | 9/2012 | Reschiglian et al. | |
| 8,470,180 B2 | 6/2013 | Leonard et al. | |
| 2002/0084221 A1 | 7/2002 | Verkaart et al. | |
| 2002/0195152 A1 * | 12/2002 | Fernandes | B01L 3/502707 |
| | | | 137/803 |
| 2003/0175947 A1 * | 9/2003 | Liu | B01F 11/0071 |
| | | | 435/288.5 |
| 2004/0019300 A1 | 1/2004 | Leonard | |
| 2004/0072278 A1 * | 4/2004 | Chou | B01L 3/502761 |
| | | | 435/29 |
| 2004/0094733 A1 * | 5/2004 | Hower | A61B 5/14514 |
| | | | 251/11 |
| 2005/0045479 A1 * | 3/2005 | Weigl | B01F 5/0646 |
| | | | 204/603 |
| 2005/0136545 A1 * | 6/2005 | Schmid | B01L 3/50273 |
| | | | 436/45 |
| 2005/0148064 A1 | 7/2005 | Yamakawa et al. | |
| 2007/0099289 A1 * | 5/2007 | Irimia | B01F 13/0066 |
| | | | 435/287.2 |
| 2012/0234731 A1 | 9/2012 | Senftleber | |
| 2012/0301903 A1 * | 11/2012 | Putnam | G01N 21/05 |
| | | | 435/7.92 |
| 2013/0065017 A1 * | 3/2013 | Sieber | B41J 2/14129 |
| | | | 428/137 |
| 2013/0086980 A1 | 4/2013 | Gadini et al. | |
| 2015/0165346 A1 * | 6/2015 | Puleo | B01D 21/0087 |
| | | | 210/695 |
| 2015/0166956 A1 | 6/2015 | Puleo et al. | |

OTHER PUBLICATIONS

Assidjo et al., "Osmolarity Effects on Red Blood Cell Elution in Sedimentation Field-Flow Fractionation", Journal of Chromatographic Science, pp. 229-236, vol. 37, Issue 7, Jul. 1999.
Zheng et al., "Membrane Microfilter Device for Selective Capture Electrolysis and Genomic Analysis of Human Circulating Tumor Cells", J Chromatogr A, pp. 154-161, vol. 1162, Issue 2, Aug. 2007.
Brune et al., "Quality, Stability and Safety Data of Packed Red Cells and Plasma Processed by Gravity Separation Using a New Fully Integrated Hollow-Fibre Filter Device", Advances in Hematology, pp. 1-6, vol. 2010, 2009.
Roda et al., "Field-Flow Fractionation in Bioanalysis A Review of Recent Trends", Analytica Chimica Acta, pp. 132-143, vol. 635, Issue 2, Mar. 2009.
Kersaudy-Kerhoas et al., "Validation of a Blood Plasma Separation System by Biomarker Detection", Lab on a Chip, pp. 1587-1595, vol. 10, Issue 12, 2010.
Gossett et al., "Label-Free Cell Separation and Sorting in Microfluidic Systems", Anal Bioanal Chem, pp. 3249-3267, vol. 397, Issue 8, Aug. 2010.
Dimov et al., "Stand-Alone Self-Powered Integrated Microfluidic Blood Analysis System (SIMBAS)", Lab on a Chip, pp. 845-850, vol. 11, Issue 5, 2011.
Bhagat et al., "Pinched Flow Coupled Shear-Modulated Inertial Microfluidics for High-Throughput Rare Blood Cell Separation", Lab on a Chip, pp. 1870-1878, vol. 11, Issue 11, 2011.
Lim et al., "Visualization of Microscale Particle Focusing in Diluted and Whole Blood Using Particle Trajectory Analysis", Lab on a Chip, pp. 2199-2210, vol. 12, Issue 2, 2012.
Udara R. Dharmasiri, "Highly Efficient Selection, Enumeration, Enrichment, and Molecular Profiling of Low-Abundant Biological Cells", 202 Pages.
C. Galligan et al., "Mesoscale Blood Cell Sedimentation for Rapid Collection of Millilitre Samples", Electronic Supplementary Material (ESI) for Lab on a Chip. This journal is © The Royal Society of Chemistry 2015, 7 Pages.

(56) References Cited

OTHER PUBLICATIONS

C. Galligan et al.,"Mesoscale blood cell sedimentation for processing millilitre sample volumes", This journal is © The Royal Society of Chemistry 2015, Received Jun. 10, 2015, Lab Chip, 2015, 15, 3274-3277.

* cited by examiner

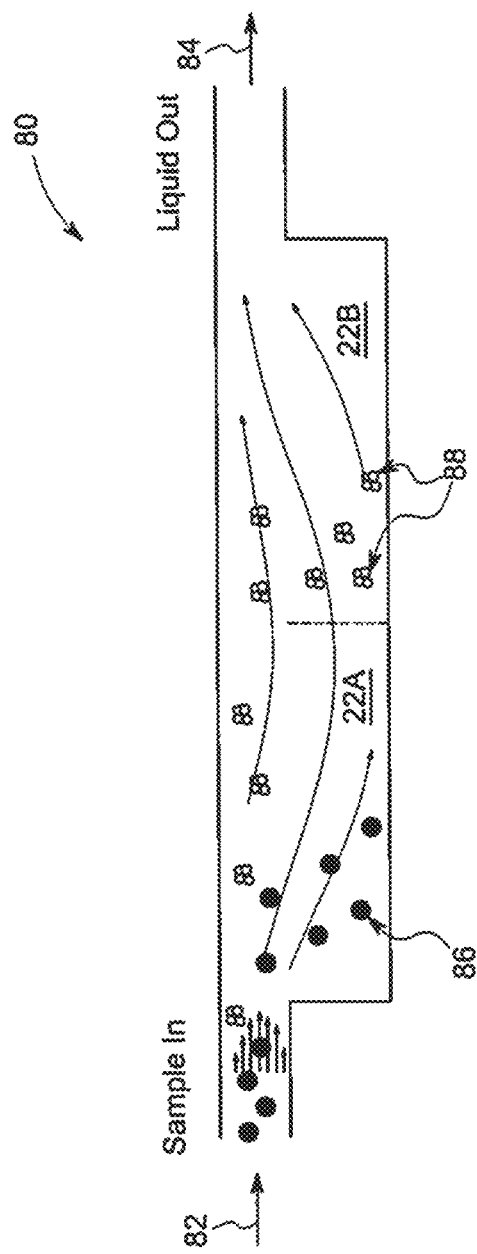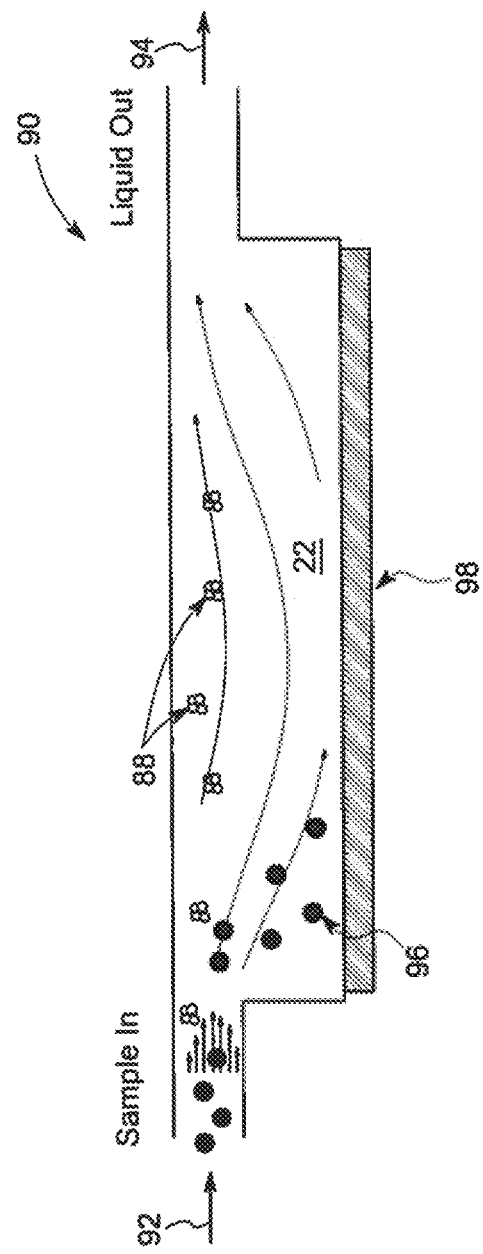

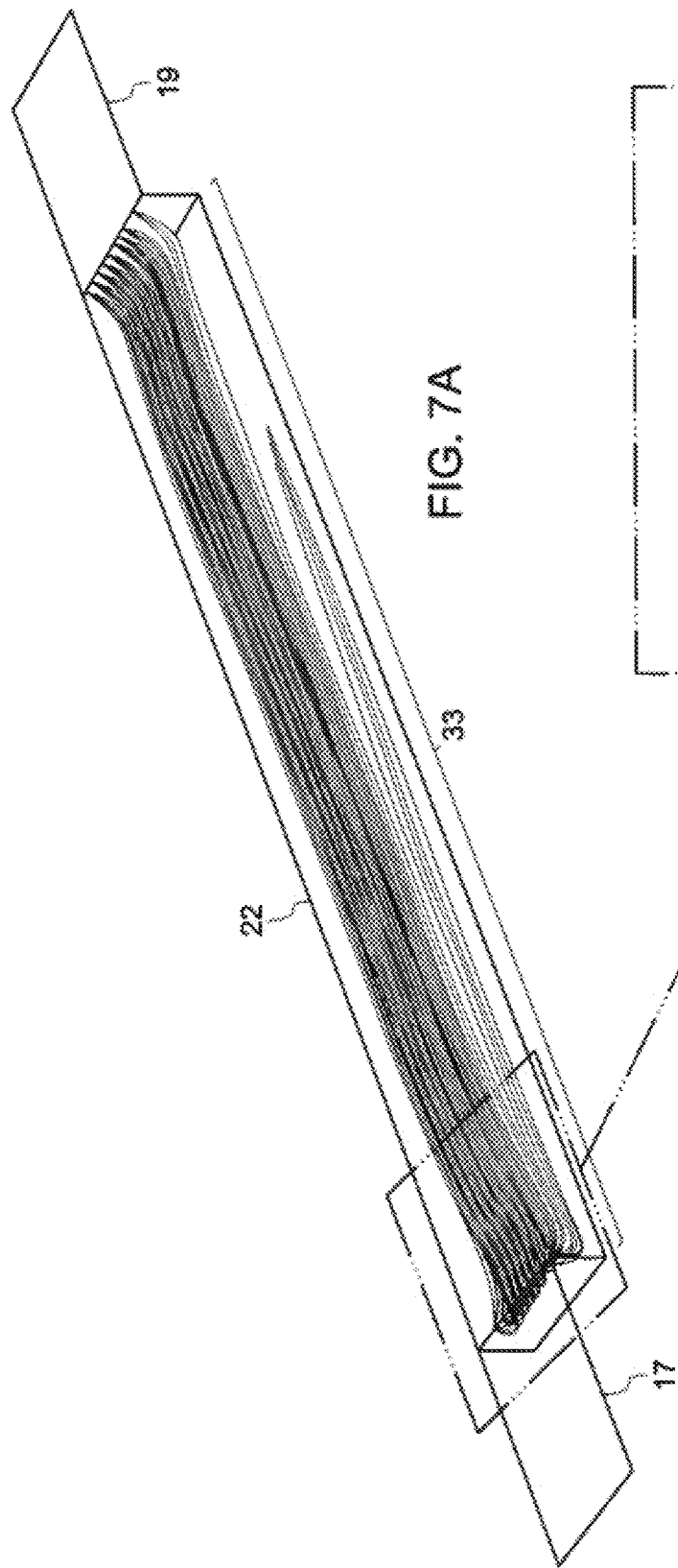
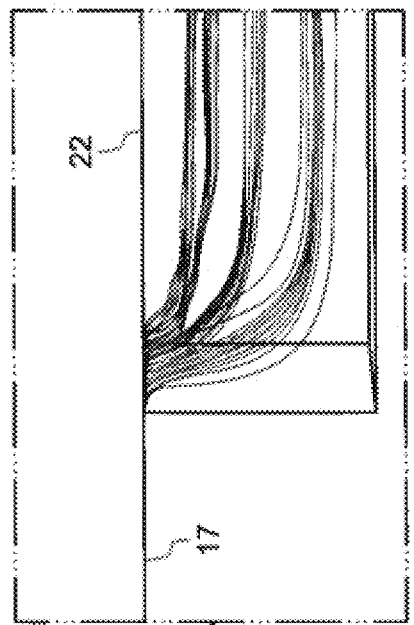
FIG. 7A
FIG. 7B

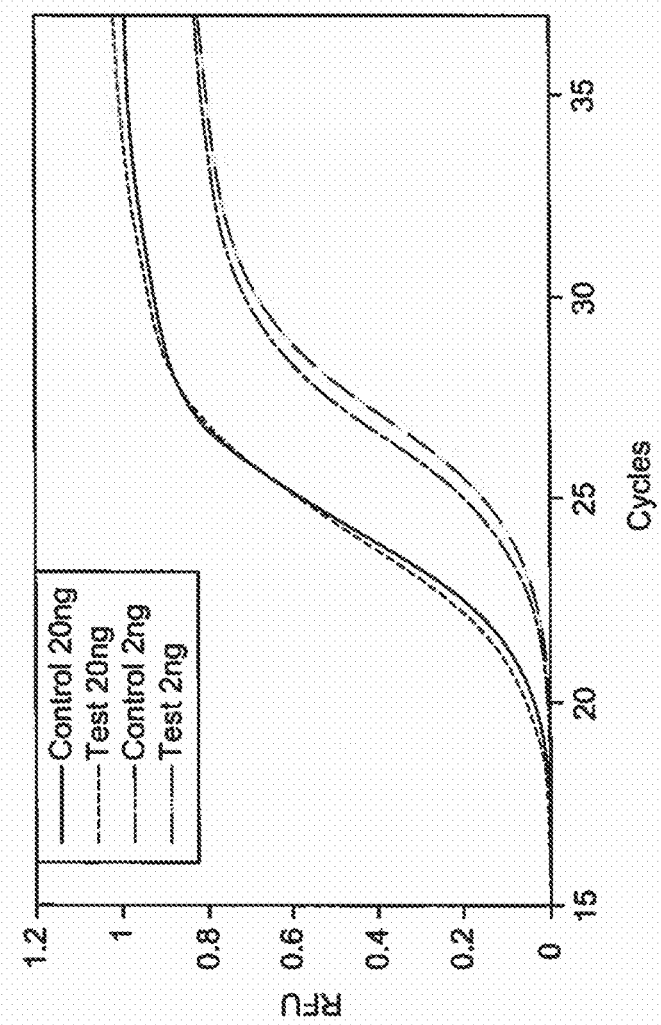
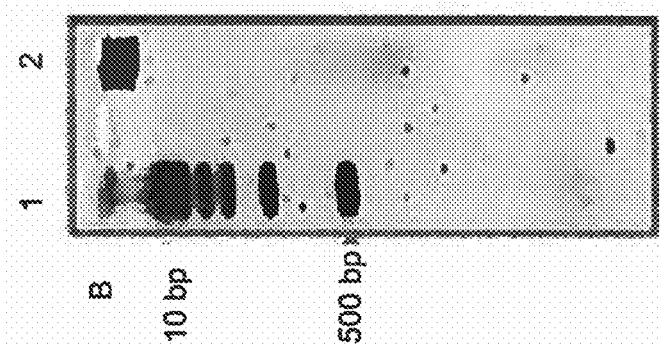
FIG. 8C
FIG. 8D

DEVICES FOR SEPARATION OF PARTICULATES, ASSOCIATED METHODS AND SYSTEMS

CROSS REFERENCE TO RELATED APPLICATIONS

This application is a continuation in part claims the benefit of U.S. application Ser. No. 14/167,393, titled "Devices for separation of particulates, associated methods and systems", filed on Jan. 29, 2014, now copending, which is incorporated herein by reference.

SEQUENCE LISTING

The instant application contains a Sequence Listing which has been submitted electronically in ASCII format and is hereby incorporated by reference in its entirety. Said ASCII copy, created on Aug. 1, 2016, is named 268069A SL.txt and is 761 bytes in size.

FIELD

The application relates to systems and devices comprising microfluidic and mesofluidic channels useful for separating particulate materials from fluids using fluidic expansions in the devices or systems. In a particular aspect, the application relates to a method for separating particulates using the systems, and devices provided herein.

BACKGROUND

Preparation and manipulation of high quality cells or biomolecules are primary requirements for a variety of diagnostic or therapeutic applications. Though filtration techniques are commonly used for capturing cells, they pose various challenges including the inability to obtain high separation efficiencies for heterogeneous cell populations, clogging of pores or harsh filtration conditions causing cellular damage. The challenges are exacerbated when filtering larger volumes of crude biological samples. In addition to filtration, a number of microfluidic separation techniques exist that rely on the application of a force, which acts to push or pull cells in a direction perpendicular to the direction of flow of the sample fluid being processed. Several of these continuous flow techniques may be useful in efficiently separating out cells from blood, including hydrodynamic filtration, inertial and deterministic lateral flow separation. However, in other embodiments the method may require pre-dilution of the blood sample and are limited to relatively low volumetric flow rates.

Recent developments on "filter-free" mechanisms for biological sample preparation offer portable purification devices for limited volumes. Primary applications have been in point-of-care diagnostics, where relatively small samples are collected and directly processed within the collection vessel. However, there remains a need to expand these simple separation methods to larger volumetric flow rates to provide alternatives to large scale centrifugation and filtration techniques.

A continuous flow separation technique is field flow fractionation (FFF) in which differential retention of particulates being eluted through a microchannel results in separation of particulates having different characteristics. However, the relevance of FFF for whole blood separation remains uncertain as FFF often requires relatively dilute starting blood samples. While combinations of separation techniques, such as hydrodynamic filtration and inertial focusing, have increased throughput limits associated with continuous flow separations. These "high throughput" implementations require carefully controlled flow rates and/or upstream sample pre-filtration or dilution.

Sedimentation-based devices may provide simpler methods of cell and/or particulate separation from fluids containing them without the need for careful fluid flow control and/or excessive sample dilution. However, there exists a need to provide devices and methods that enable high-speed separation of particulates such as cells and/or dispersed particulates from fluids containing them without the need to augment sedimentation rates via capital intensive equipment, such as centrifuges. A fast and efficient separation and collection of particulates or cells from a large sample volume without complex equipment is an unmet need. Therefore, inexpensive devices that can accelerate particulate separation via sedimentation, and enable use of a large sample volume with minimal human intervention are highly desirable.

BRIEF DESCRIPTION

In one embodiment, the present application provides a separation device for separating particulates dispersed within a base fluid and having a relative density difference compared to the base fluid. The separation device comprises a first microchannel and a mesofluidic collection chamber. The first microchannel has a length $l_1$ and a height $h_1$, wherein the length $l_1$ is in a range from about 5 millimeters to about 100 millimeters, and wherein the first microchannel comprises a fluid inlet. The mesofluidic collection chamber has a first side and a second side, wherein the mesofluidic collection chamber is operatively coupled to the first microchannel on the first side, having a first fluid outlet at the second side, such that the fluid inlet, first microchannel, and the first fluid outlet are in a fluidic communication via the mesofluidic collection chamber, wherein the mesofluidic collection chamber has a height $h_3$, and wherein the height $h_3$ is in a range from about 0.1 centimeter to about 0.8 centimeter. In this embodiment of the device, the particulates dispersed in the base fluid traverse through the first microchannel under an influence of a force field, and wherein the particulates delaminate from the base fluid in the first microchannel and trace a fluidic expansion while entering to the mesofluidic collection chamber, and at least a portion of the particulates in a portion of the base fluid are sedimented in the mesofluidic collection chamber.

In another embodiment, a system is provided herein. The system comprises an input chamber and an output chamber; and (b) a separation device for separating particulates dispersed within a base fluid and having a relative density difference compared to the base fluid. The separation device comprises a first microchannel and a mesofluidic collection chamber. The first microchannel has a length $l_1$ and a height $h_1$, wherein the length $l_1$ is in a range from about 5 millimeters to about 100 millimeters, and wherein the first microchannel comprises a fluid inlet. The mesofluidic collection chamber has a first side and a second side, wherein the mesofluidic collection chamber is operatively coupled to the first microchannel on the first side, and wherein the mesofluidic collection chamber comprises a first fluid outlet at the second side, such that the fluid inlet, first microchannel, and first fluid outlet are in fluidic communication via the mesofluidic collection chamber. The mesofluidic collection chamber has a height $h_3$, and wherein the height $h_3$ is in a range from about 0.1 centimeter to about 0.8 centimeter. In this embodiment of the system, the input chamber is operatively coupled to the first microchannel via the fluid inlet, and the output chamber is operatively coupled to the mesofluidic collection chamber via the first fluid outlet; wherein the particulates dispersed in the base fluid traverse through the first microchannel under an influence of a force field, and wherein the particulates delaminate from the base fluid in the first microchannel and trace a fluidic expansion while entering to the mesofluidic collection chamber, and at least a portion of the particulates in a portion of the base fluid are sedimented in the mesofluidic collection chamber.

In another embodiment, a method for separating particulates dispersed within a base fluid and having a relative density difference compared to the base fluid is provided. The method comprises providing a separation device comprising: a first microchannel and a mesofluidic collection chamber. In the separation device, the first microchannel has a length $l_1$ and a height $h_1$, wherein the length $l_1$ is in a range from about 5 millimeters to about 100 millimeters, and wherein the first microchannel comprises a fluid inlet. The mesofluidic collection chamber has a first side and a second side, wherein the mesofluidic collection chamber is operatively coupled to the first microchannel on the first side, and wherein the mesofluidic collection chamber comprises a first fluid outlet at the second side, such that the fluid inlet, first microchannel, and first fluid outlet are in fluidic communication via the mesofluidic collection chamber. The mesofluidic collection chamber has a height $h_3$, wherein the height $h_3$ is in a range from about 0.1 centimeter to about 0.8 centimeter. The particulates dispersed in the base fluid traverse through the first microchannel under an influence of a force field, and wherein the particulates delaminate from the base fluid in the first microchannel and trace a fluidic expansion while entering to the mesofluidic collection chamber, and at least a portion of the particulates in a portion of the base fluid are sedimented in the mesofluidic collection chamber. The method also comprises introducing a sample of an unprocessed fluid comprising the particulates dispersed within the base fluid in the first microchannel via the fluid inlet; flowing the unprocessed fluid under a determined fluid flow regime in the separation device, wherein the fluid flow regime comprises a first fluid flow having a first linear velocity enable particulate delamination in the first microchannel, a second fluid flow having a second linear velocity enable sedimentation of the delaminated particulates in the mesofluidic collection chamber, and the second linear velocity is a fraction of the first linear velocity. The step of introducing the sample of an unprocessed fluid is followed by separating at least a portion of the particulates from a portion of the unprocessed fluid by sedimenting the portion of the particulates in the mesofluidic collection chamber; recovering at least a portion of the sedimented particulates from the mesofluidic collection chamber; and collecting a stream of a processed fluid devoid of the particulates initially present in the base fluid at the first fluid outlet.

One embodiment of a method for separating cells dispersed within a base fluid of whole blood sample, comprises providing a separation device comprising: a first microchannel and a mesofluidic collection chamber. In the separation device, the first microchannel has a length $l_1$ and a height $h_1$, wherein the length $l_1$ is in a range from about 5 millimeters to about 100 millimeters, and wherein the first microchannel comprises a fluid inlet. The mesofluidic collection chamber has a first side and a second side, wherein the mesofluidic collection chamber is operatively coupled to the first microchannel on the first side, and wherein the mesofluidic collection chamber comprises a first fluid outlet at the second side, such that the fluid inlet, first microchannel, and first fluid outlet are in fluidic communication via the mesofluidic collection chamber. The mesofluidic collection chamber has a height $h_3$, wherein the height $h_3$ is in a range from about 0.1 centimeter to about 0.8 centimeter. The particulates dispersed in the base fluid traverse through the first microchannel under an influence of a force field, and wherein the particulates delaminate from the base fluid in the first microchannel and trace a fluidic expansion while entering to the mesofluidic collection chamber, and at least a portion of the particulates in a portion of the base fluid are sedimented in the mesofluidic collection chamber. The method also comprises the step of introducing a sample of a whole blood comprising the blood cells dispersed within the plasma in the first microchannel via the fluid inlet. The step of introducing sample is followed by flowing the whole blood under a determined fluid flow regime in the separation device, wherein the fluid flow regime comprises a first fluid flow having a first linear velocity enable particulate delamination in the first microchannel, a second fluid flow having a second linear velocity enable sedimentation of the delaminated particulates in the mesofluidic collection chamber, and the second linear velocity is a fraction of the first linear velocity. The method also comprises separating at least a portion of the blood cells from the whole blood by sedimenting the portion of the particulates in the mesofluidic collection chamber; recovering at least a portion of the blood cells initially present in the whole blood sample from the mesofluidic collection chamber; and collecting a stream of the processed blood plasma at the first fluid outlet.

DRAWINGS

These and other features, aspects, and advantages of the present invention will become better understood when the following detailed description is read with reference to the accompanying drawings in which like characters represent like parts throughout the drawings, wherein:

FIG. 5 illustrates a method of separating particulates from a fluid using one embodiment of the devices.

FIG. 6 illustrates a method of separating particulates from a fluid using one embodiment of the devices.

FIG. 7A is an image taken from computational fluid dynamic (CFD) models showing fluid flow pattern through the device. FIG. 7B is a perspective side view of the fluid flow pattern through the device as shown in FIG. 7A.

FIG. 8C illustrates performance characteristics of a cell separation device, showing amplification of DNA extracted from the cells captured by the within the mesofluidic collection chamber of the present device.

FIG. 8D illustrates performance characteristics of a cell separation device, showing an image of gel electrophoresis of cell-free (circulating) DNA extracted from the plasma collected to the output chamber.

DETAILED DESCRIPTION

Figure 1A:
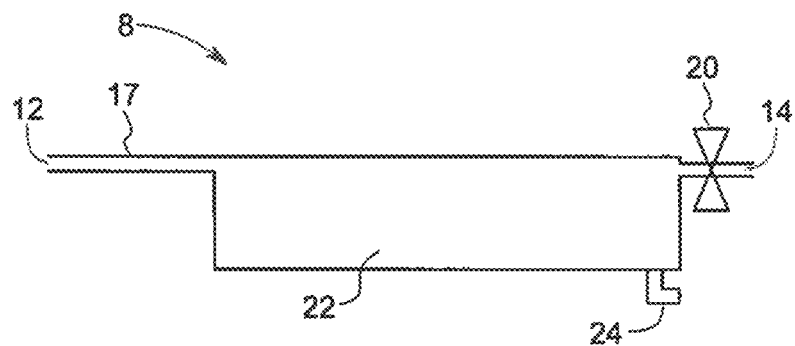
FIG. 1A is a schematic drawing of side view of a device suitable for use in one embodiment of the devices.

Separation of particulates dispersed within a base fluid (collectively "the unprocessed fluid"), for example separation of blood cells dispersed within blood plasma, or separation of particulate impurities dispersed in water, may be effected using various embodiments of systems, devices and methods provided by the present application. Embodiments of the device and its device components (e.g. FIGS. 1A-1B) comprise a fluid inlet for introducing the unprocessed fluid into the device, a first fluid outlet for removing processed fluid from the device, and a separation region comprising a first microchannel, and a mesofluidic collection chamber, disposed between the fluid inlet and the first fluid outlet. The particulates are separated from the base fluid of the unprocessed fluidic sample using expansion of fluidic flow from the microchannel to the mesofluidic collection chamber and sedimentation. This is unlike a filtration device that relies entirely on physical barriers to filter particulates and standard microfluidic separation device that lack capacity for separating particulates from large volume and/or high fluid flow rates.

To more clearly and concisely describe the subject matter of the disclosed application, the following definitions are provided for specific terms, which are used in the following description and the appended embodiments. Throughout the specification, exemplification of specific terms should be considered as non-limiting examples.

The terms "particulate" and "particle", and their plural referents "particulates" and "particles", are used interchangeably herein and are intended to have the same meaning, particle being treated as a synonym for particulate. As used herein, the term "particles" refers to a portion of the fluidic sample loaded into the device, which excludes the base fluid. The term "particles" includes without limitation cells, inorganic colloids, polymers, biopolymers, immiscible liquids, heterogenous solids, and nominally gaseous/liquid materials in a solid phase. For example, blood cells, grains of sand, oil droplets, nucleic acids, or ice crystals are all particles.

As used herein, the term "operationally generates" refers to a function of generating one or more fluid flow regimes through the microchannel and through the mesofluidic collection chamber during operation of the device. For example, when a fluid sample is loaded into the device and flows through the microchannel for separation of the particulates from the base fluid, the fluidic expansion from a microchannel to a mesofluidic collection chamber generates a field of flow with fluid flow regimes under the operating conditions of the device.

As used herein, the term "fluidic sample" or "unprocessed fluid sample" refers to a mixture that comprises a non-fluid component and a fluid component. The mixture may be heterogeneous or homogenous in nature. The loaded sample is interchangeably used herein with a "fluidic sample" or "unprocessed fluid sample". In some embodiments, the "unprocessed fluid sample" refers to a fluid that comprises a base fluid and particulates dispersed within the base fluid. In the unprocessed fluid sample, the particulates have a relative density difference compared to the base fluid. The sample may comprise without limitation, a fluid comprising one or more particulates, a fluid comprising one or more cells, water with particulates, water-oil emulsion, or a fluid with impurities. For example, a sample comprises a slurry of sand and water, or a fluidic sample comprises cells and plasma. The term "fluidic sample" is used interchangeably and without limitation with the term "dispersion", "particulate dispersion", or "cellular dispersion" when identifying a generic class of fluidic sample. In some embodiments, a cellular dispersion refers to a sample of cells dispersed in a fluid, for example blood cells dispersed in plasma, cells dispersed in a growth medium, or cells dispersed in a stabilization medium.

As used herein, the term "base fluid" refers to a portion of the fluidic sample which excludes the particulates. For example, a whole blood sample comprises blood cells in plasma, wherein the plasma is a base fluid. For another example, an aqueous sand dispersion comprises sand in water, wherein water is a base fluid.

As used herein, the term "processed fluid" refers to a fluid that is generated from an unprocessed fluid loaded to the present device. The processed fluid is enriched in the base fluid and depleted in the particulates initially present in the unprocessed fluid or fluid sample loaded to the device.

As used herein, the term "relative density difference" refers to a difference between the density of the particulates present in the base fluid and the density of the base fluid.

As used herein, the term "delamination" refers to the act of driving particulates into a specific laminate of a fluid flow containing multiple layers within a channel.

As used herein, the term "sediment" refers to particulate motion induced by an applied force field. Motion or movement of particulates in a fluid in response to a force may be active or passive, and the movement is referred to herein as sedimentation. For example, in cases where the force of gravity augments the action of an externally applied electric field in inducing particulate movement. Sedimentation usually provides a simple means of separating particulates from a base fluid. In one embodiment, in an aqueous sand dispersion, the sand particulates have a density greater than that of the base fluid and sediment in the direction of the gravitational field. In another embodiment, in an oil-in-water emulsion, the oil droplets have a density less than that of the base fluid and transit in the direction opposing the gravitational field. In another embodiment, in a dispersion of magnetic particulates, the magnetic particulates sediment in the direction of an applied magnetic field. In another embodiment, in a dispersion of charged particulates, the charged particulates differentially sediment based on their polarity within an applied electric field.

As used herein, the term "fines" refer to fine particulates, which are undesirable resin or resin particles of lower quality. For example, misshapen, broken/crushed or fragmented resin particles. Generally, presence of these fine particles in a resin interferes chromatographic separation of different molecules, such as proteins, using the resin.

The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The device, system and method of the present application demonstrate usage of hydrodynamic entrance effects for an efficient separation of particulates from a large volume of sample into a mesoscale collection chamber (such as a mesofluidic collection chamber). The structure of the device comprising a microfluidic channel and a mesofluidic collection chamber provides a technique that is compatible with equipment-free, point of care (POC) separation device. For example, for plasma separation, the equipment-free, point of care (POC) separation device further minimizes or eliminates the challenges associated with storage and shipment of the unprocessed whole blood sample for remote sample collection.

In certain embodiments, a separation device is configured to separate particulates present in an unprocessed fluid sample. The unprocessed fluid sample may comprise particulates dispersed in a base fluid, where the particulates have a relative density difference compared to the base fluid. In some of these embodiments, the separation device for separating particulates from the base fluid comprises a first microchannel and a mesofluidic collection chamber. In some of these embodiments, the first microchannel comprises a fluid inlet, and the mesofluidic collection chamber comprises a first fluid outlet. The first microchannel has a length $l_1$ and a height $h_1$, where the length $l_1$ is in a range from about 5 millimeters to about 100 millimeters. The mesofluidic collection chamber has a first side and a second side, wherein the mesofluidic collection chamber is operatively coupled to the first microchannel on the first side, having a first fluid outlet at the second side, such that the fluid inlet, first microchannel, and the first fluid outlet are in a fluidic communication via the mesofluidic collection chamber. The mesofluidic collection chamber has a height $h_3$ in a range from about 0.1 centimeter to about 0.8 centimeter. In operation, in this embodiment of the separation device, the particulates dispersed in the base fluid traverse through the first microchannel under an influence of a force field. In this embodiment, at least a portion of the particulates delaminate from the base fluid in the first microchannel and subjected to a fluidic expansion while entering the mesofluidic collection chamber. At least a portion of the particulates in a portion of the base fluid are sedimented in the mesofluidic collection chamber.

Figure 1B:
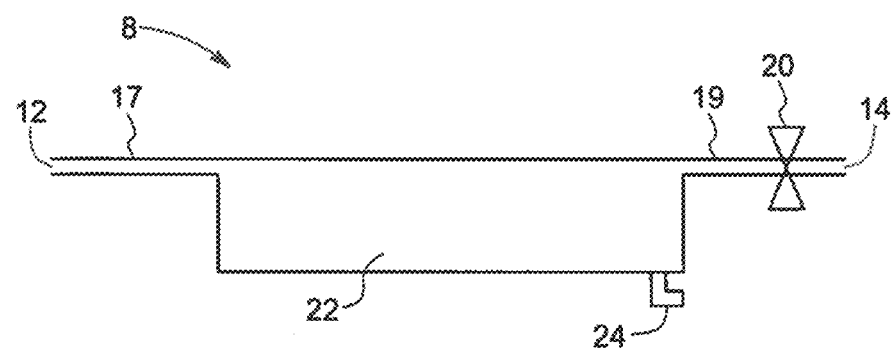
FIG. 1B is a schematic drawing of front view of a device suitable for use in one embodiment of the devices.
Figure 1C:
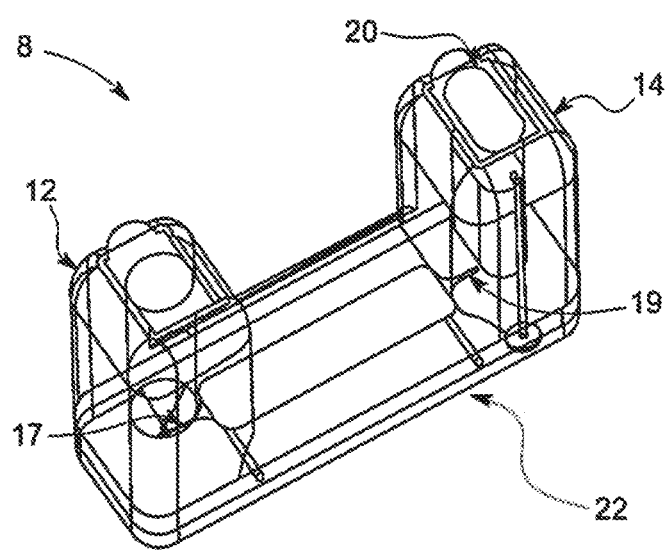
FIG. 1C is a schematic drawing of a perspective view of a device suitable for use in one embodiment of the devices.

In some embodiments, the device further comprises a second microchannel having a second fluid outlet disposed at the second side of the mesofluidic collection chamber, such that the fluid inlet, first microchannel, second microchannel, and second fluid outlet are in a fluidic communication via the mesofluidic collection chamber. The second microchannel has length $l_2$ in a range from about 5 millimeters to about 100 millimeters and a height $h_2$. The first microchannel and the second microchannel comprise one or more walls. The fluid inlet and the second fluid outlet may be present, without limitation at the ends of the channel. The second microchannel may not be required if the length of the mesofluidic collection chamber is increased, without limiting device function. Non-limiting examples of an embodiment of the device are shown in FIGS. 1A, 1B and 1C.

Advantageously, the separation device enables rapid particulate stratification in the first microchannel while maintaining large volume capacity in the mesofluidic collection chamber, thereby drastically increasing the capacity and throughput of the separation device of the present application as compared to existing microfluidic plasma separators.

The first microchannel or second microchannel may also be referred to as a "microfluidic channel" since at least one of the dimensions of the microchannel is appropriately measured in microns (about 10 microns to about 100 microns). In various embodiments of the device, the first microchannel has a length $l_1$ and a height $h_1$. In some embodiments of the device, the second microchannel has a length $l_2$ and a height $h_2$. In some embodiments, the first microchannel and the second microchannel are disposed horizontally. The first microchannel and second microchannel are configured to allow the flow of a fluid at a predetermined flow rate. The device may be set for a specific flow rate as desired before operating the device.

Typically, the first microchannel and second microchannel have lengths appropriately measured in units larger than microns, for example millimeters (mm), centimeters (cm) or meters (m). In one or more embodiments, the length $l_1$ of the first microchannel is in a range from about 5 mm to about 100 mm. In some embodiments of the device, the first microchannel has length $l_1$ in a range from about 5 mm to about 70 mm. In yet another embodiment, the first microchannel has length $l_1$ in a range from about 10 mm to about 25 mm. In some other embodiments of the device, length $l_1$ of the first microchannel is in a range from about 15 mm to about 67 mm.

In one or more embodiments, the second microchannel has a length $l_2$ in a range from about 5 mm to about 100 mm. In some embodiments of the device, the second microchannel has length $l_2$ in a range from about 5 mm to about 70 mm. In yet another embodiment, length $l_2$ of the second microchannel is in a range from about 10 mm to about 25 mm. In another embodiment, the second microchannel has length $l_2$ in a range from about 15 mm to about 67 mm.

In some embodiments, the microchannels, such as the first microchannel and second microchannel, may be of similar shape and/or height. In some embodiments, both of the first microchannel and the second microchannel are of same shape, such as cylindrical. Further, both of the first microchannel and second microchannel may be of uniform height. The each of the microchannels may be of different shapes, such as one is cylindrical and the other is rectangular. In some other embodiments, the first microchannel and the second microchannel are of different shapes. By way of example, the first microchannel is of cylindrical shape wherein the second microchannel is of rectangular shape. In some embodiments, the first microchannel and the second microchannel are of average height of $h_1$. In some embodiments, each of the microchannels may be of an irregular shape, for example, a channel defined in part by an undulating wall, and may be characterized by a plurality of heights. In various embodiments of the device, the first microchannel has a height $h_1$. In one or more embodiments, the second microchannel has a height $h_2$. In some embodiments, both of the first microchannel and the second microchannel have same height, so that $h_1$ and $h_2$ are same.

In one embodiment, the average height $h_1$ of the first microchannel is in a range from about 1 to about 1000 microns (μm). In an alternate embodiment, the average height $h_1$ of the first microchannel is in a range from about 10 to about 500 microns. In yet another embodiment, the average height $h_1$ of the first microchannel is in a range from about 20 to about 250 microns.

In one embodiment, the height $h_2$ of the second microchannel is in a range from about 1 to about 1000 micron. In an alternate embodiment, the height $h_2$ of the second microchannel is in a range from about 10 to about 500 micron. In yet another embodiment, the height $h_2$ of the second microchannel is in a range from about 20 and about 250 micron.

As noted, the device comprises a mesofluidic collection chamber. The first microchannel is disposed between the fluid inlet and the mesofluidic collection chamber. The second microchannel is disposed between the mesofluidic collection chamber and the second fluid outlet. The device is configured to receive a fluid, the fluid enters the device via the fluid inlet as unprocessed fluid. The unprocessed fluid includes a base fluid and particulates. The unprocessed fluid is processed as the unprocessed fluid travels through the length $l_1$ of the first microchannel and the particulates in a portion of the base fluid enter the mesofluidic collection chamber. Subsequently, the processed fluid exits from the fluid outlet of the device. Subsequently, the processed fluid exits from the fluid outlet of the device. During the passage of fluid between the fluid inlet to the first/second fluid outlet, particulates in at least a portion of the base fluid flow out of the first microchannel and enter into the mesofluidic collection chamber under the influence of the fluid flow through the first microchannel and one or more additional forces, such as the ambient gravitational field, an applied force field, or buoyancy forces. The interactions of the particulates within the first microchannel, the interactions of the particulates with the bottom of the first microchannel and a fluidic expansion from the first microchannel to the mesofluidic collection chamber enable rapid sedimentation and capture (retaining the particulates in the mesofluidic collection chamber) of the particulates in the mesofluidic collection chamber, as compared to gravity sedimentation alone. The capture of particulates in the mesofluidic collection chamber refers to retaining the particulates in the mesofluidic collection chamber.

As noted above, the fluid inlet, first microchannel, second microchannel, and second fluid outlet are in a fluidic communication via the mesofluidic collection chamber. The portion of the mesofluidic collection chamber where the particulates are sedimented (or captured) is referred to herein as a "separation area". It may be noted that the separation area is defined when the fluid inlet and the mesofluidic collection chamber are in fluidic communication via the first microchannel. In one example, the mesofluidic collection chamber collects the cells from a whole blood sample, which is loaded to the device through the fluid inlet.

In some embodiments, the sedimentation process starts in the first microchannel, when a portion of the particulates interacts with the bottom of the first microchannel. The sedimentation process for those particulates in a portion of the base fluid may complete in the mesofluidic collection chamber. The sedimented particulates are entrapped (or captured) within the mesofluidic collection chamber, which is also known as particulate capture by the device. The particulates, which are captured (sedimented) to the mesofluidic collection chamber are collected by various means. The capture efficiency of the particulates is at least dependent on the length of the first microchannel, time of residence of the particulates to the first microchannel, and height of the mesofluidic collection chamber.

As noted, "capture efficiency" refers to a probability function, dependent on the average number of particulates interacting with the bottom surface of the first microchannel during transit through the first microchannel to the mesofluidic collection chamber and the probability of particulate to enter the mesofluidic collection chamber for each such interaction.

Figure 15:
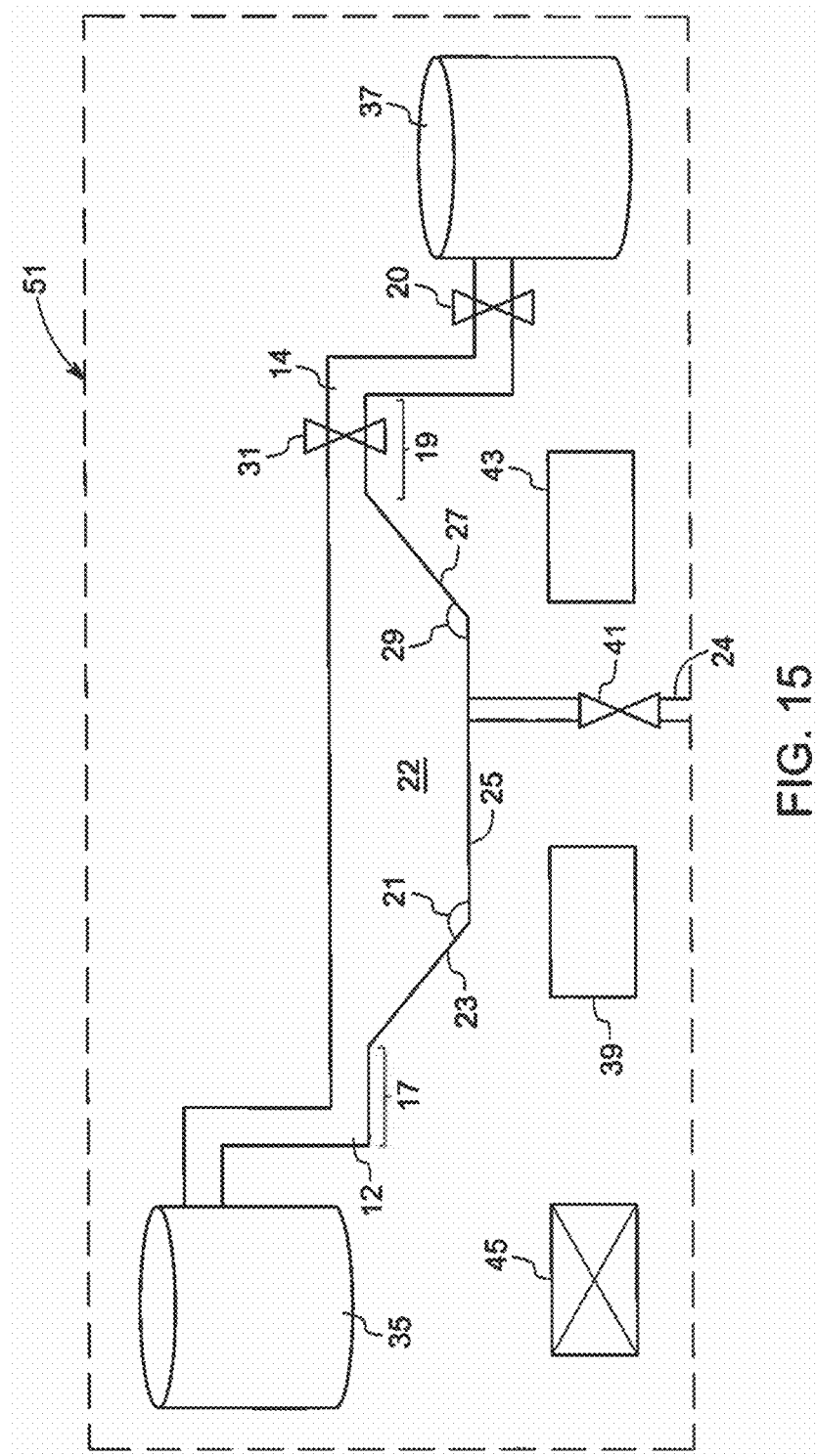
FIG. 15 illustrates a schematic representation of front view of an embodiment of the system for separating particulates.

The mesofluidic collection chamber may be of different shapes. The mesofluidic collection chamber has at least three walls, first wall at the first side of the mesofluidic collection chamber, second wall at the second side of the mesofluidic collection chamber and third wall is the bottom wall. In one or more embodiments, the mesofluidic collection chamber comprises an angle of collection 21, such as $\alpha_1$, which is formed between the first wall 23 and the bottom wall 25 of the mesofluidic collection chamber. In some embodiments, an angle 29 between the second wall 27 and the bottom wall 25 may be $\alpha_2$ (as shown in FIG. 15). In some embodiments, the $\alpha_1$ and $\alpha_2$ are same. In some other embodiments, the $\alpha_1$ and $\alpha_2$ are different. In some embodiments, the $\alpha_1$ and $\alpha_2$ are in a range from about 90° to about 170°. In some other embodiments, the $\alpha_1$ and $\alpha_2$ are different, such as $\alpha_1$ is 90° and $\alpha_2$ is 170°. In one or more examples, the mesofluidic collection chamber is rectangular in shape, wherein the angles $\alpha_1$ and $\alpha_2$ of the mesofluidic collection chamber are 90°.

The mesofluidic collection chamber has a height $h_3$. In some embodiments, the height $h_3$ of the mesofluidic collection chamber is in a range from about 2 mm to about 20 mm. In some embodiments, the height $h_3$ of the mesofluidic collection chamber is in a range from about 3 mm to about 15 mm. In some other embodiments, the height $h_3$ of the mesofluidic collection chamber is in a range from about 4 mm to about 10 mm. The height of the mesofluidic collection chamber $h_3$ has significant contribution towards the capture efficiency of the device. The height of the mesofluidic collection chamber ($h_3$) is referred to herein as a critical height ($h_3$).

The separation device is configured to receive unprocessed fluid sample having the base fluid and particulates dispersed in the base fluid. The unprocessed fluid enters the separation device through the fluid inlet and traverses through the first microchannel under an influence of a force field, such as gravitational field or an electric field. At least a portion of the particulates delaminate from the base fluid in the first microchannel and generate lamellar flow lines such as upper, middle and lower flow lines (as shown in FIG. 7B), wherein the delamination refers to the act of driving particulates into a specific laminate of a fluid flow containing multiple layers within a channel. The lamellar flow lines expand from the first microchannel to the mesofluidic collection chamber. The particulates are preferentially concentrated into the lower lamellar flow lines within the first microchannel. The concentration of the particulates to the lower lamellar flow line drives the particulates towards the bottom surface of the mesofluidic collection chamber. As the particulates pass from the first microchannel to the mesofluidic collection chamber, the particulates sediment into the bottom of the lamellar flow lines and the particulate-distribution is altered compared to the original distribution at the fluid inlet. Upon entering the mesofluidic collection chamber, the concentrated particulates at the bottom of the lamellar flow lines are driven toward the bottom of the mesofluidic collection chamber as a function of fluid flow rate within the device and relative height of the mesofluidic collection chamber compared to that of the first microchannel.

Sedimentation of particulates to lower flow lines within the first microchannel acts as a high speed concentrator of particulates in the mesofluidic collection chamber and decreases the transit time required to capture the particulates. The particulates trace a fluidic expansion while entering the mesofluidic collection chamber from the first microchannel. At least a portion of the particulates in a portion of the base fluid move towards the bottom of the mesofluidic collection chamber due to prior delamination in the first microchannel and are captured at the bottom of the mesofluidic collection chamber due to sedimentation.

In some embodiments, the device is configured such that a fluid flow regime is generated in at least a portion of the device, where the fluid flow regime comprises a first flow regime established in the first microchannel and a second flow regime is established in the mesofluidic collection chamber. The second flow regime is characterized by a lower overall flow rate (second linear velocity) than the flow rate of the first flow regime (first linear velocity). The second flow rate is a fraction of the first flow rate.

The microchannel is a channel into which the particulates dispersed in a base fluid are introduced. As noted, the first microchannel comprises a fluid inlet through which the unprocessed fluid enters to the first microchannel and then proceeds to the mesofluidic collection chamber. In one embodiment, the fluid inlet is configured to receive and hold the unprocessed fluid sample comprising particulates dispersed within a base fluid. The fluid sample may be delivered to the first microchannel using a device component. In one example, a vacuum line may be coupled to the first/second fluid outlet to deliver the unprocessed fluid sample in the first microchannel under the influence of vacuum. The unprocessed fluid sample may include a biological sample, a water sample or an oil sample. The fluid follows lamellar flow lines in the first microchannel. The second microchannel comprises a second fluid outlet, through which the processed fluid is exiting from the separation device may be collected at the second fluid outlet, for example in an output chamber.

A simple relationship between the critical height ($h_3$) and residence time ($t_R$) accounts for much of the performance variance in the device. The residence time refers to an average time spent by the fluid in the mesofluidic collection chamber. In particular, the residence time is total duration of time of interaction of the particulates with the bottom of the mesofluidic collection chamber as well as with other particulates in the mesofluidic collection chamber. The critical height ($h_3$) of the device is the largest determinant of device performance. Efficient particle separation is achieved when the critical height $h_3$ is matched to the settling characteristics of a particulate. A relationship between the critical height $h_3$ and particle settling characteristics is established by a series of experiments, wherein the devices with mesofluidic collection chamber of varying depths were employed. A transfer function was established that accounts for 99.4% of the performance variability and determines the relationship between residence time and critical height for a monodispersed sample of 2 μm silica particles. The experimental results were used to generate the transfer function and the regression statistics. A time to capture (referred to herein as capture time) particulates in the mesofluidic collection chamber was calculated using Stoke's settling velocity and the critical height for each experiment.

In various runs using the device prototypes with varying critical height show the trend in capture efficiency which reflects the trend in capture time compared to the residence time. The highest capture efficiency was determined when the residence time was closest to the particle capture time at a given critical height (Run 3). Conversely, the lowest capture efficiency was determined when the residence time was much shorter than the theoretical particle capture time (Runs 1, 2, and 4), as shown in Table 1. The effect of critical height ($h_3$) of the device, total volume capacity (V) of the device, residence time ($t_R$), volumetric flow rate through the device (F), on the capture efficiency, turbidity of the unprocessed fluid sample (turbidity IN), turbidity of the processed fluid (turbidity OUT) and theoretically derived capture time are provided in Table 1 after detailed analysis of eight (8) different device prototypes. Additional factors contribute to particle capture in the device beyond particle settling velocity including edge effects, dead volumes of the device, variable critical height as the mesofluidic collection chamber fills with sediment, length of the first microchannel, and the presence of a microporous sieve.

TABLE 1

Effect of critical height and residence time on the capture efficiency.

| Device prototype | $h_3$ (cm) | V (cc) | $t_R$ (sec) | F (ml/min) | Turbidity in (NTU) | Turbidity out (NTU) | Capture efficiency (%) | Capture time (sec) |
|---|---|---|---|---|---|---|---|---|
| 1 | 0.6 | 2.4 | 480 | 0.3 | 656 | 364 | 45 | 1775 |
| 2 | 0.6 | 2.4 | 240 | 0.6 | 759 | 387 | 49 | 1775 |
| 3 | 0.2 | 0.8 | 480 | 0.1 | 679 | 58 | 91 | 600 |
| 4 | 0.6 | 2.4 | 360 | 0.4 | 822 | 464 | 44 | 1775 |
| 5 | 0.4 | 1.6 | 240 | 0.4 | 717 | 426 | 41 | 1183 |
| 6 | 0.2 | 0.8 | 240 | 0.2 | 534 | 204 | 62 | 600 |
| 7 | 0.4 | 1.6 | 480 | 0.2 | 717 | 306 | 57 | 1183 |
| 8 | 0.2 | 0.8 | 360 | 0.13 | 633 | 137 | 78 | 600 |

The mesofluidic collection chamber has a length $l_3$. In some embodiments, the mesofluidic collection chamber has a length $l_3$ in a range from about 1 centimeter (cm) to about 25 centimeter (cm). In some embodiments, the mesofluidic collection chamber has a length $l_3$ in a range from about 2 cm to about 10 cm. In some other embodiments, the mesofluidic collection chamber has a length $l_3$ in a range from about 2 cm to about 5 cm. In one example embodiment, the mesofluidic collection chamber has a length $l_3$ of about 4 cm. In this embodiment, the device may be used for small scale application, such as for purifying whole blood sample to generate plasma. In another example embodiment, the mesofluidic collection chamber has a length $l_3$ of about 23 cm. In this embodiment, the device may be used for a large scale application, such as for harvesting cells from the medium in bioprocess application.

The device may be configured, such that the average time required for the particulates to sediment to the mesofluidic collection chamber (height $h_2$) is less than the time required for the particulates to transit across the length $(l_1+l_2+l_3)$ of the device, which includes the length of the first microchannel $l_1$, the length of the second microchannel $l_2$ and the length of the mesofluidic collection chamber $l_3$. The particulate capture efficiency and/or volumetric throughput may be improved by increasing the length $l_1$ of the first microchannel and/or decreasing the height $h_1$ of the microchannel. An increase in length $l_1$ of the first microchannel increases the time available for the particulates to interact with the bottom lamellar flow line of the first microchannel, which further results in increasing the capture efficiency (see Table 2).

The particulates that are captured, also referred to as "sediment" in the mesofluidic collection chamber, are collected using one or more outlets, these outlets may be referred to herein as "collection-outlets" 24 (FIG. 1A, 1B, FIG. 15). The mesofluidic collection chamber further comprises one or more collection-outlets, which are employed for recovering a portion of the particulates collected or captured in the mesofluidic collection chamber. A collection-outlet may be connected to a conduit or a syringe to retrieve the particulates from the mesofluidic collection chamber of the device. In some embodiments, the collection-outlet may be used for removing captured particulates in large volume batches of unprocessed fluid sample to prevent filling up the collection chamber. The collection-outlet may also be used to increase the separation efficiency. In absence of collection-outlets, the mesofluidic collection chamber may be filled up rapidly, which results in directing the particulates in the base fluid to the fluid outflow through the first fluid outlet or second fluid outlet instead of capturing. This decreases the capture efficiency of the separation device. In one or more embodiments, a pump may be coupled to the one or more collection-outlets to recover the captured particulates from the mesofluidic collection chamber during the operation. For example, in the case of a whole blood sample, the separated blood cells are recovered from the mesofluidic collection chamber using a tube or syringe for downstream applications.

In some embodiments, the separation device further comprises particulate traps positioned in the bottom of the mesofluidic collection chamber. The "particulate traps" generally refer to additional smaller wells added to the mesofluidic collection chamber. The collected particulates in the mesofluidic collection chamber allows some convective flushing of the collection chamber without loss of particulates. In some embodiments, the particulate traps are a series of smaller well at the bottom surface of the collection chamber that measured the width of the collection chamber (~20 mm) by 0.5 mm, with a depth of 1 mm About 25 of these additional traps were added to the bottom of the collection chamber, which allowed additional convective flushing of the collection chamber without loss of particulates.

Optionally, the particulates, cells or other materials present in the fluidic sample may be collected or captured in the mesofluidic collection chamber and described herein as "captured particulates" or "captured cells". The captured particulates or captured cells may be recovered from the mesofluidic collection chamber of the device, which are described at times herein as "recovered particulates" or "recovered cells". In some embodiments, the recovery of particulates or cells is less than 100%, wherein the number of captured particulates or captured cells in the mesofluidic collection chamber is different than the number of recovered particulates or recovered cells.

The device further comprises a microporous body disposed on the mesofluidic collection chamber. In some embodiments, the microporous body is a microporous surface. In one embodiment, the microporous body constitutes one wall defining the mesofluidic collection chamber. The microporous body may be a membrane or a solid body through which holes have been created. In one or more embodiments, the microporous body comprises pores originating at a first surface of the microporous body and terminating at a second surface of the microporous body. For example, pores traversing a film may be created by chemical etching techniques and/or laser ablative techniques.

The term "microporous" is used herein because the pores have dimensions appropriately measured in microns. In one embodiment, the pores have an average diameter between about 1 micron and about 500 microns. In an alternate embodiment, the pores have an average diameter between about 10 microns and about 250 microns. In yet another embodiment, the pores have an average diameter between about 20 microns and about 100 microns. In one embodiment, the porosity of the microporous body is between about 10 and about 75 percent. In an alternate embodiment, the porosity of the microporous body is between about 20 and about 65 percent. In yet another embodiment, the porosity of the microporous body is between about 30 and about 60 percent.

As noted, in one embodiment, the microporous body may be a microporous film such as a monofilament screen or mesh made from, for example, polyester, nylon, polypropylene. Alternatively, the microporous body may be a chemically-etched KAPTON, titanium, or NiTinol film. In one embodiment, the microporous body is a laser etched organic film made from an organic polymeric material such as KAPTON.

In some embodiments, the mesofluidic collection chamber is covered with a microporous surface. In an exemplary embodiment, each of the microchannels (first and second) is rectangular in shape and is defined on three sides by walls enclosing the microchannel and the two microchannels are connected with a microporous body. Typically, the mesofluidic collection chamber is configured such that every pore of the microporous body enables direct fluid communication between the microchannel and the mesofluidic collection chamber. In some embodiments, the particulates are sedimented and pass through the pores of the microporous surface and are trapped within the mesofluidic collection chamber. In one or more embodiments, the device further comprises an applied force field across one or more dimensions of the first and/or second microchannel, for example across the height of the first and/or second microchannel to cause the particulates to be collected in the mesofluidic collection chamber.

In various embodiments, the separation of particulates from the base fluid occurs as the unprocessed fluid sample is flowing through the device for processing. Having traversed the microporous body, the particulates in the base fluid continue to migrate away from the microporous body and then move towards the bottom of the mesofluidic collection chamber under the influence of the passive and/or active forces.

The results from initial trials using silica particles are represented in Table 2. The results clearly show that the capture efficiency is increased using length of the first microchannel ($l_1$) of the device. The results also reflect the fact that the addition of the microporous membrane cover on the mesofluidic collection chamber influences cell capture. While the first microchannel concentrates particles in the lowest flow lines of the fluid flow regime, the microporous membrane increases the total fraction of flow directed to the bottom portions of the mesofluidic collection chamber and interferes with cell escape. A number of experiments demonstrated the enhancements provided by incorporating both inlet/outlet microchannels and a microporous sieve. Capture efficiencies for 2 μm particles with various device configurations are presented in Table 2. The devices were configured to have a 4×1×0.2 cm collection chamber and were run at a residence time of 240 s. Microchannel lengths were varied at inlet and outlet between 0 and 66.5 mm. The presence of a 40 μm microporous mesh was also varied within the device. The baseline capture efficiency for a device with neither microchannels nor a microporous sieve was 60% (Prototype 9). Adding an inlet microchannel with varying length resulted in increased capture efficiencies of up to 81% at the arbitrary limit set on device length (Prototypes 11). The presence of a microporous sieve also increased capture efficiencies up to 81% at the arbitrary limit set on device length (Prototype 12, Table 2).

TABLE 2

| Capture Efficiency of particulates (2 micron) in different device structure. | | | |
|---|---|---|---|
| Device prototype | Length of microchannels ($l_1/l_2$) (mm) | Microporous body | Capture Efficiency (%) |
| 9 | 0/0 | − | 60 |
| 10 | 16.5/16.5 | − | 71 |
| 11 | 66.5/16.5 | − | 81 |
| 12 | 16.5/16.5 | + | 81 |

In one or more embodiments, the device further comprises one or more controllers for altering one or more of the external force field, a first linear velocity of a fluid flow through the first microchannel, a second linear velocity of a fluid flow through the mesofluidic collection chamber. The terms "linear velocity" and "flow rate" are interchangeably used herein.

In some embodiments, the device further comprises an input chamber operatively coupled to the first microchannel via the fluid inlet. Additionally or alternatively, in some embodiments, the device further comprises an output chamber operatively coupled to mesofluidic collection chamber through the first fluid outlet. The processed fluid after separation of at least a portion of the particulates from the base fluid flows out through the mesofluidic collection chamber to the first fluid outlet; which is further connected to the output chamber.

In some other embodiments, the device further comprises an output chamber operatively coupled to the second microchannel via the second fluid outlet. In these embodiments, the mesofluidic collection chamber is connected to the input chamber through the first microchannel, and the mesofluidic collection chamber is connected to the output chamber through the second microchannel. The unprocessed fluid sample is loaded to the input chamber, which enters the first microchannel through the fluid inlet and is processed while subsequently traversing a portion of the first microchannel and the mesofluidic collection chamber. The processed fluid after separation of at least a portion of the particulates from the base fluid flows out through the second microchannel to the second fluid outlet and to the output chamber.

In some embodiments, the input chamber may be a bioreactor. In some of these embodiments, the unprocessed fluid sample may include the cultured cells in a medium. The unprocessed fluid sample is passed through the device for separation of cells from the culture medium. In these embodiments, after separation of cells, the medium is collected in the output chamber, wherein the output chamber may function as a waste chamber or downstream processing chamber.

In some other embodiments, an unprocessed sample is a whole blood sample, wherein the whole blood sample is added to the input chamber. The whole blood is passed through the device, blood cells are collected to the mesofluidic collection chamber, and the plasma that is substantially devoid of blood cells is passed through the second microchannel and collected in the output chamber. In these embodiments, the processed sample is plasma, collected to the output chamber and can be retrieved for various downstream applications.

In some embodiments, the device further comprises a first fluid driver, such as a pump. In these embodiments, the first fluid driver may be configured to facilitate a flow of the base fluid having the particulates through the first microchannel and to extract at least a portion of a processed fluid from the second microchannel, wherein the processed fluid is enriched in the base fluid and depleted in the particulates. In an exemplary embodiment, a pump is coupled to the first or second fluid outlet for recovering the processed fluid. In some other embodiments, a pump is coupled to the output chamber to recover the collected fluid after processing through the device. For example, when a whole blood sample is used as an unprocessed sample fluid, the processed base fluid (plasma) after separating blood cells is collected in the output chamber. The processed plasma may be recovered by using a pump coupled to the output chamber. The processed fluid, such as plasma may also be retrieved by coupling a pump to the first or second fluid outlet.

In some or different embodiments, the device further comprises a second fluid driver configured to recover at least a portion of the particulates collected in the mesofluidic collection chamber. In these embodiments, the mesofluidic collection chamber is coupled to the second fluid driver, such as a pump to recover at least a portion of the particulates from the mesofluidic collection chamber during operation. For example, when a whole blood sample is used as an unprocessed sample fluid, the blood cells separated from the base fluid (plasma) are collected in the mesofluidic collection chamber. These blood cells may be recovered from the mesofluidic collection chamber by using one or more pumps.

In some embodiments, one or more of the input chamber, the fluid inlet, the second fluid outlet, the first microchannel, the second microchannel, the mesofluidic collection chamber, and the output chamber are configured to be coupled to an analytical device. In embodiments where the sample is a biological sample, the analytical device may include, but is not limited to, a cell-analyzer, a spectrophotometer, a fluorescence spectrophotometer, and a fluorescence activated cell sorter.

In one or more embodiments, a force field causes the particulates to migrate through the device. In embodiments of the device, the particulates dispersed within the base fluid traverse through the first microchannel under an influence of an applied force field. In one or more embodiments, the device further comprises an applied force field across one or more dimensions of the first and/or second microchannel, for example across the height $h_1$ of the first and/or second microchannel to cause the particulates to sediment into the mesofluidic collection chamber. The applied force field may function across the height $h_1$ of the first and/or second microchannel under operating conditions of the device. The applied force field may facilitate reduction in the amount of time required for the particulates to pass through the first microchannel by moving the fluid at relatively high flow rate through the first microchannel to sediment the particulates in the mesofluidic collection chamber. The particulates are trapped within the mesofluidic collection chamber, wherein the fluid flow rate is relatively low.

In one example, the force field may be ambient gravity at times herein referred to as "ambient gravitational forces". In one embodiment, the separation device is configured such that the ambient gravitational force acts across the height $h_1$ of the first microchannel and causes particulates dispersed within the base fluid to sediment into the mesofluidic collection chamber.

In some embodiments, the applied force field is an external force field. In these embodiments, the external force causes the particulates to sediment in the mesofluidic collection chamber. In one or more embodiments, the applied force field may include, but is not limited to, a magnetic field, an electric field, an electrophoretic field, and acoustic field. In an alternate embodiment, the applied force field may be a combination of the ambient gravitational forces present together with the external force field, such as an applied electric field or magnetic field. In an alternate embodiment, the forces causing the particulates to migrate across the microchannel, or the microporous body or the mesofluidic collection chamber are exerted by the fluid being processed. For example, buoyancy forces may dominate gravitational forces in the separation of oil in water emulsions.

In some embodiments, the device comprises one or more controllers for controlling a force field, wherein the force field may be an external force field, such as magnetic field or electric filed. In one embodiment, a controller may be coupled to an electrical field and modulates the field strength as per requirement of the device.

The particulates along with the base fluid traverse through at least a portion of the separation device under the influence of passive and/or active forces. Further, while traversing, the particulates interact with the bottom of the first microchannel and are separated from the base fluid. The interactions of the particulates with the bottom of the first microchannel decrease the linear velocity of those particulates and initiate sedimentation of those particulates into the mesofluidic collection chamber.

In certain embodiments, a plurality of particulates have a relative density difference when compared to the base fluid. The relative density difference, at least in part, enables the particulates to sediment to the mesofluidic collection chamber. The separation of particulates using the device and the associated methods, at least in part, is based on sedimentation of the particulates. The selective sedimentation of particulates present in a heterogeneous mixture containing multiple types of particulate having relative density (settling velocity) differences among particles and base fluid may be utilized for the present device.

Sedimentation is one of the simplest methods of cell or particulate separation, wherein the separation is based on the density and size of the particulate itself. However, sedimentation is typically only thought of as a useful method of high speed cell separation if coupled to a centrifuge and/or density gradient medium (DGM). In some cases, sedimentation rates are too low to be useful for applications, such as blood cell separation from plasma, or separation of particulate impurities from water. Thus, separation of particulates using the ambient gravitational field or natural particulate buoyancy at useful rates has remained an objective.

In the device of the present application, the force which causes the particulates to traverse through the mesofluidic collection chamber may be an active force such as an applied electric field, a passive force such as the ambient gravitational field, or a combination thereof. For example, gravitational field augments action of an externally applied electric field to induce movement or sedimentation of the particulate.

Figure 2B:
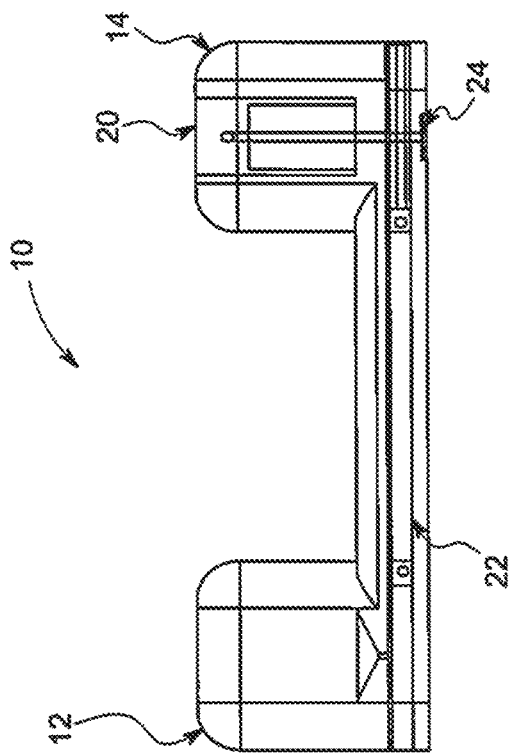
FIG. 2B is a schematic drawing of side view of a device suitable for use in one embodiment of the devices.
Figure 2C:
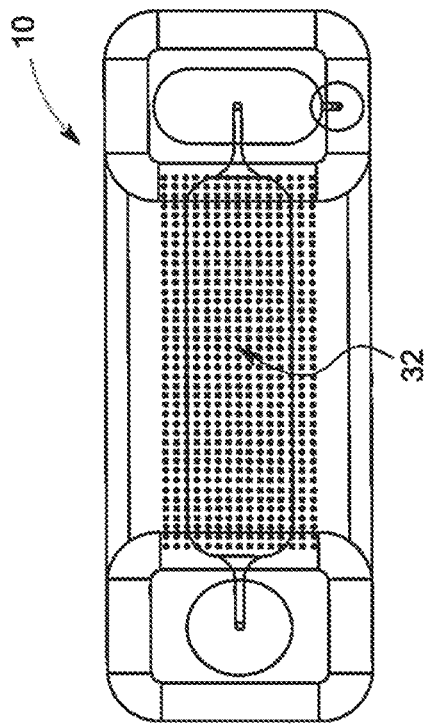
FIG. 2C is a schematic drawing of top view of a device suitable for use in one embodiment of the devices.
Figure 2A:
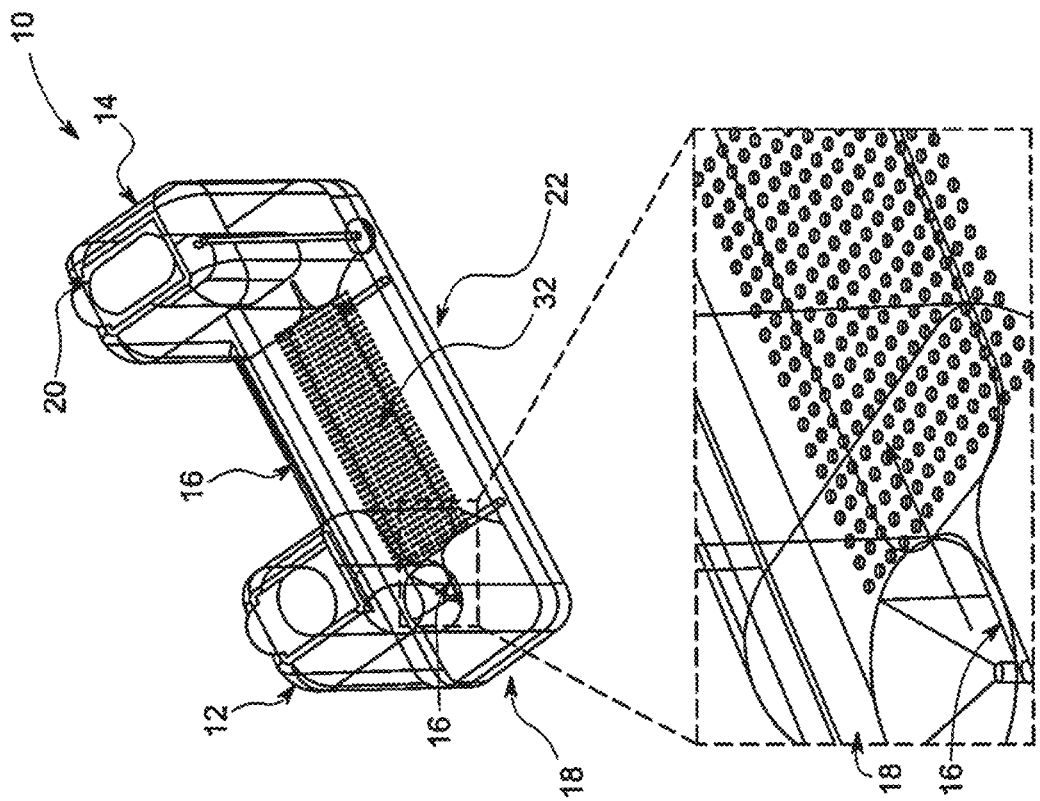
FIG. 2A is a schematic drawing of front view of a device suitable for use in one embodiment of the devices. A magnified perspective view of a portion of the device illustrating a microchannel and a microporous surface is reproduced in a dotted-lined rectangular block.

In the device of FIGS. 2A to 2C, the sedimentation rate of the particulates in suspension is proportional to the centrifugal force applied to the particulates, as represented by Equation 1:

$$v = \frac{d^2(\rho_p - \rho_l)}{18\eta} \times g_c$$

where v is the sedimentation rate, d is the diameter of the particulate, $\rho_p$ is the density of the particulate, $\rho_l$ is the density of the DGM, η is the viscosity of the DGM, and $g_c$ is the centrifugal force. In the case where the centrifugal force is simply equal to gravity, sedimentation of blood components is slow with erythrocytes settling at ~1 micron/s. Previously, this has limited the utility of the earth's gravitational field (g) for high speed, sedimentation-based cell separation, and necessitated the equipment intensive centrifugation approach. As an example, centrifugal forces of 10-800×g are typically applied to blood to separate out specific cell types, which are stratified across the DGM. With the application of the excess centrifugal force, separation can take place on the order of minutes. A simpler and automated separation is enabled by the claimed device that can use only the earth's gravitational field to achieve similar separation rates. It should be noted that other forces would follow a similar relationship where centrifugal, or gravitational force fields could be substituted without limitation for magnetic, electric, or dielectric fields.

The unprocessed fluid sample loaded in the device may be processed such that the particulates from an unprocessed fluid sample may be separated and enter into the mesofluidic collection chamber, where the particulates may sediment. In a non-limiting example, the device may be used to separate oil from water, where oil may sediment in the mesofluidic collection chamber.

The fluid that flows through the first microchannel and emerges at the second fluid outlet after removal of at least a portion of the particulates in the unprocessed fluid sample may be recovered from the device's second fluid outlet. The fluid recovered from the second fluid outlet may be referred to herein as "processed sample" and/or "processed fluid". In some embodiments, the processed sample may be a sample of interest. For example, the processed water sample recovered after removal of the particulates is purified water, which is a sample of interest. In some other embodiments, the processed sample may be a waste product.

In one or more embodiments, the device is configured to separate particulates from one or more of whole blood, cells in culture medium, a cell extract, a tissue extract, a petroleum product, or water. In one bioprocess application, the unprocessed fluid sample may include cells in a cell-culture medium, the device may be used to separate the cells from the culture medium. The cells collected in the mesofluidic collection chamber are further retrieved for downstream applications. In another bioprocess application, the unprocessed fluid sample may be cell extract or tissue extract.

In addition to particulate collection, the device may be configured to distinguish particulates with respect to size, sedimentation velocity, or density. The particulates with different size may be separated using the device. The particulates having different sedimentation velocity may also be separated using the device. In some embodiments, the particulates have an average diameter between 1 and 250 microns. As the microporous surface comprises pores with an average diameter in a range of 1 to 500 microns, the particulates that are smaller than the pore size pass through the microporous surface.

In one or more embodiments, the device is configured to selectively separate particles in a suspended medium based on size range. In these embodiments, the particles are resin particles for use in chromatography application. In one embodiment, the resin particles are smaller than a predetermined range of particle size, such as cells or other biomolecules. In some embodiments, the mixture of resin particles and cultured cells may be used as an unprocessed fluid sample.

In some embodiments, the device may further be used for differential sedimentation based on sedimentation velocity rather than size of the particles. For example, a resin mixed with cells cultured in a medium may be used as an unprocessed fluid sample. In these embodiments, a resin is directly added to the unprocessed fluid sample, which includes cells in the culture media and biomolecules produced by the cells (e.g. proteins). The biomolecules may include, proteins bound to the added resin. Due to relatively higher settling velocity of the resin particles (with bound protein), the resin particles are sedimented faster than the cells from the unprocessed fluid sample. The resin-bound proteins are sedimented and collected to the mesofluidic collection chamber. The cells in the culture media are collected to the output chamber as a waste. This method of differential sedimentation using the single device is advantageous over the current processes. The current processes typically remove cells from the unprocessed fluid sample (i.e. debulking) by depth filtration, enzyme application or mechanical procedures prior to use the fluid including biomolecules (proteins) through a chromatography column containing resin to capture the biomolecules. Additional steps may be used to purify proteins from the protein-bound resin retrieved from the mesofluidic collection chamber. The recovered protein form the resin may be used for different downstream applications. In other embodiments, the resin after eluting the proteins may be re-used for other binding applications. The differential sedimentation using the present device helps avoid many of the expenses and challenges related to the current cell clarification or debulking processes and chromatography applications.

In the case of purification of cells from a whole blood sample, the plasma generated as "processed sample" is collected to the output chamber and the sample of interest may be the recovered as blood cells. In some other examples, the processed plasma may be a sample of interest, depending on the user requirement. The plasma generated is substantially depleted with blood cells and can be used for plasma preparation for required applications. In one or more embodiments, the processed sample is collected from the device outlet, wherein the outlet is coupled to a pump to drive out the processed sample.

In applications pertaining to cell-free plasma analysis, device configuration and processing parameters may be used to desirably affect a capture efficiency and level of dilution of the collected plasma. The mesofluidic collection chamber is typically primed with buffer solution, which in turn results in dilution of the base fluid. For example, in instances where the unprocessed fluid is a blood sample, the plasma may be diluted due to presence of the buffer solution, a level of plasma dilution varies with input volume of the unprocessed blood sample as well as with the size of the mesofluidic collection chamber. Reducing the volume of the mesofluidic collection chamber reduces the required amount of initial priming buffer, and thereby increases the final concentration of base fluid, such as plasma, that is collected at the output chamber. Since the size of the mesofluidic collection chamber dictates the volume of cells that may be captured, the design of the device may be optimized to balance dilution of the base fluid with respect to the processing capacity. By way of example, the design of the device may be modified to provide desirable level of plasma dilution and blood processing capacity The plasma dilution is primarily a function of device design and size of the mesofluidic collection chamber. Plasma collection efficiency may also be dependent on factors other than the device design and size of the mesofluidic collection chamber. This is due to the ability to add an additional volume of buffer to the input chamber (after the primary blood sample is passed through the device), which pushes/extracts plasma trapped within the mesofluidic collection chamber leaving the trapped cells behind. In table 3, this is labelled as the post-blood buffer flush. This flush results in more plasma collected from the sample (specifically, cell free portions of the plasma), however this flush also leads to an additional dilution of the collected plasma with the buffer. Table 3 demonstrates variations in plasma collection efficiency and plasma dilution with respect to device design in presence or absence of a post-blood buffer flush.

At step 1, the device is primed with a buffer solution prior to introduction of a whole blood sample into the input chamber. In particular, the mesofluidic collection chamber is primed with the buffer solution. At step 2, at least a portion of the whole blood sample is introduced in the input chamber of the device. At step 3, the whole blood sample fed to the device is passed at least through portions of the device, as a result, at least a portion of the cells (and/or particulates) settle down at the bottom of the mesofluidic collection chamber, while non-cellular portions of the plasma (such as, but not limited to, cell-free nucleic acid) remain evenly distributed throughout the mesofluidic collection chamber. However, initially, at the output chamber no plasma is initially collected, as the priming buffer is closest to the mesofluidic collection chamber and enters first to the chamber. Next, at step 4, once a volume of the whole blood sample loaded in the device is at least equivalent to the volume of the mesofluidic collection chamber, the whole blood sample is run through the device and plasma begins to enter the output chamber (while the sedimented cells remain in the bottom). Plasma collection continues at step 4, until there is a minimal or zero amount of whole blood sample that is present in the input chamber. In instances where the amount of whole blood sample present in the input chamber or the device is much smaller than the volume of the mesofluidic collection chamber, a substantial portion of plasma may be left in the device (see the first two rows in table 3). In these instances, an additional buffer volume may be added to the input chamber (step 5) to increase the overall volume of the sample to an extent that allows the sample to run through the device. Adding additional buffer to collect remaining plasma in the left over whole blood sample facilitates collection of the remaining plasma in the output chamber, while minimizing or preventing contamination of the plasma from the sedimented cells.

It was noted that this volumetric calculation of plasma (table 3) in blood sample is limiting as diffusive mixing of particulates (cells) in the base fluid (plasma) due to plug flow model of the fluid within the mesofluidic collection chamber typically alters the exact timing of the plasma to reach the output chamber and the volume required for 100% plasma collection. However, the results (table 3) show that a large amount of cell-free nucleic acid can be collected using these steps and the plasma collection efficiency can be increased by running additional buffer through the system. In addition, it is noted that the rapid processing speeds within the present device (0.5 mL/min and above) is dependent on cell trapping immediately upon hitting the bottom surface of the mesofluidic collection chamber (such that sedimentation of one "critical height" causes irreversible cell capture). The effective capture does not appear to be due to aggregation of cells (e.g., red blood cells which are known to aggregate at low shear rates); however, capture efficiencies were similar using the same device for both cells and silica particles (data in table 1 and 2).

TABLE 3

Results of processing a blood sample through the device

| Initial volume of plasma in blood sample (ml) | Mesofluidic collection chamber volume (ml) | Post blood buffer flush (ml) | Total solution collected (ml) | Actual Plasma collected (ml) | % Plasma concentration | % Plasma recovery |
| --- | --- | --- | --- | --- | --- | --- |
| 0.25 | 0.5 | 0 | 0.25 | 0 | 0 | 0 |
| 0.5 | 0.5 | 0 | 0.5 | 0 | 0 | 0 |
| 1 | 0.5 | 0 | 1 | 0.5 | 50 | 50 |
| 1 | 0.5 | 0 | 2 | 1.5 | 75 | 75 |
| 0.25 | 0.5 | 0.5 | 0.75 | 0.25 | 33 | 100 |
| 0.5 | 0.5 | 0.5 | 1 | 0.5 | 50 | 100 |
| 1 | 0.5 | 0.5 | 1.5 | 1 | 67 | 100 |
| 2 | 0.5 | 0.5 | 2.5 | 2 | 80 | 100 |
| 0.25 | 0.75 | 0.5 | 0.75 | 0 | 0 | 0 |
| 0.5 | 0.75 | 0.5 | 1 | 0.25 | 25 | 50 |
| 1 | 0.75 | 0.5 | 1.5 | 0.75 | 50 | 75 |
| 2 | 0.75 | 0.5 | 2.5 | 1.75 | 70 | 88 |
| 0.25 | 0.75 | 0.75 | 1 | 0.25 | 25 | 100 |
| 0.5 | 0.75 | 0.75 | 1.25 | 0.5 | 40 | 100 |
| 1 | 0.75 | 0.75 | 1.75 | 1 | 57 | 100 |
| 2 | 0.75 | 0.75 | 2.75 | 2 | 73 | 100 |

As shown in FIG. 1A, in one exemplary embodiment, a side view of the device 8 comprises an inlet 12, first microchannel 17, a mesofluidic collection chamber 22 and a first fluid outlet 14A. In some embodiments, a vacuum or a syringe is coupled to the collection-outlet 24 of the mesofluidic collection chamber of the device to pull a sample loaded to the device. In another embodiment, the device 8 comprises a vacuum 20 coupled to the first fluid outlet 14A of the device to pull the sample loaded to the device to a waste-tub or waste-chamber and drive the sample fluid through the device 8. In other embodiments, the fluid-flow across the device is accomplished using a positive pressure applied to the device inlet 12 for sample load. In this embodiment of the device, by increasing the length of the mesofluidic collection chamber, the capture efficiency of the device may be increased even in absence of a second microchannel.

As shown in FIG. 1B, in one exemplary embodiment, a side view of the device 8 comprises a mesofluidic collection chamber 22. In some embodiments, a vacuum or a syringe is coupled to the collection-outlet 24 of the mesofluidic collection chamber of the device to pull a sample loaded to the device. In another embodiment, the device 8 comprises a vacuum 20 coupled to the device outlet 14 to pull the sample loaded to the device to a waste-tub or waste-chamber and drive the sample fluid through the device 8. In other embodiments, the fluid-flow across the device is accomplished using a positive pressure applied to the device inlet 12 for sample load. In some embodiments, a gravity-driven flow provided through the device-inlet.

As illustrated in FIG. 1C, the device (front view) 8 comprises a fluid inlet 12, a second fluid outlet 14 and a first microchannel 17. The fluid inlet 12 is connected to the mesofluidic collection chamber 22 via a first microchannel 17. The fluid inlet 12 may at times function as and be referred to as an inlet well, which connects to the first microchannel 17. In the embodiment shown, fluid inlet 12 is configured as an inlet well in fluid communication with microchannel 17 via conduit 18. The second fluid outlet 14 is connected to the mesofluidic collection chamber 22 via a second microchannel 19.

As illustrated in FIG. 2A, the device (front view) 10 comprises a fluid inlet 12, a second fluid outlet 14 and a microchannel 16. In some embodiments, the term "microchannel" is used interchangeably with the term "separation channel". The fluid inlet 12 may at times function as and be referred to as an inlet well, which connects to the microchannel. In the embodiment shown, fluid inlet 12 is configured as an inlet well in fluid communication with microchannel 16 via conduit 18. The microchannel 16 is bounded on its lower side by microporous body 32. The device 10 also comprises a collection chamber 22 on an opposing side of the microporous body 32.

As shown in FIG. 2B, in one exemplary embodiment, a side view of the device 10 comprises a mesofluidic collection chamber 22. In some embodiments, a vacuum or a syringe 24 is coupled to the mesofluidic collection chamber 22 of the device to draw the processed fluid from the mesofluidic collection chamber 22. In another embodiment, the device 10 comprises a vacuum generator 20 coupled to the device outlet 14 provide vacuum to drive the sample fluid through the device 10 and/or to draw the sample out of the device and direct the drawn sample to a waste-tub or waste-chamber. In other embodiments, the fluid-flow across the device is facilitated by application of a positive pressure to the device inlet 12 for loading the unprocessed fluid sample. In some embodiments, a gravity-driven flow may be provided through the device-inlet. In some embodiments, a top view of the device 10 comprises a microporous surface 32, as shown in FIG. 2C.

The device enables high speed separation without using a centrifuge. In an exemplary embodiment of the device 8 or 10, a high velocity flow-stream flows across a wide sedimentation area 33 (FIG. 7A). For example, the microchannel comprises a sedimentation area of 10 mm×400 mm. In one embodiment, the flow-stream within the first microchannel 17 extends across the separation area 33, which covers the mesofluidic collection chamber 22.

In one embodiment, the sample is a whole blood sample, and the method is employed to separate one or more cell types from the whole blood sample. In this embodiment, the method comprises loading the blood sample to the device comprising two microchannels (first and second) and a mesofluidic collection chamber, contacting the blood sample to the surface of the first microchannel; generating a fluid flow regime comprising a high velocity portion flowing through the first microchannel and a low velocity portion flowing through the mesofluidic collection chamber; sedimenting the cells and capturing into the collection chamber under the applied force field and retaining a plasma fluid in the microchannel. The retained fluid is plasma, which is driven out from the device through the second fluid outlet of the second microchannel, wherein a time required for the cells to sediment is less than the time required for the cells to transit across the total length of the device.

The spreading of the fluid flow stream through the first microchannel provides a significant opportunity for interaction of the particulates with the bottom surface of the first microchannel. The addition of a static mesofluidic collection chamber 22 allowed sedimentation of the particulates into the mesofluidic collection chamber, without traversing the particulates across entire length l ($l_1+l_2+l_3$) of the device, unlike standard centrifuge tubes or large sedimentation tanks. The loss of particulates into the output chamber is minimized, which is demonstrated by showing clear plasma in FIG. 2D, step four, 48. The efficiency of the separation and the relative performance of the device compared to the filtration technology are significantly high.

One or more examples of a method for separating particulates dispersed in a base fluid and having a relative density difference compared to the base fluid are provided. The method comprises (a) providing a separation device as described above, (b) introducing a sample of an unprocessed fluid comprising the particulates dispersed within the base fluid in the first microchannel via the fluid inlet; (c) flowing the unprocessed fluid under a determined fluid flow regime in the separation device, wherein the fluid flow regime comprises a first fluid flow having a first linear velocity through the first microchannel, a second fluid flow having a second linear velocity through the mesofluidic collection chamber, wherein the second linear velocity is a fraction of the first linear velocity; (d) separating at least a portion of the particulates from a portion of the unprocessed fluid by sedimenting the portion of the particulates in the mesofluidic collection chamber; (e) recovering at least a portion of the sedimented particulates from the mesofluidic collection chamber; and (f) collecting a stream of a processed fluid devoid of the particulates initially present in the base fluid through the first fluid outlet of the mesofluidic collection chamber. In some other embodiments, where the device comprises a second microchannel, a stream of the processed fluid devoid of the particulates initially present in the base fluid are collected through the second outlet of the second microchannel. In one embodiment, the method may further comprise applying an external force field to the fluid flow of the separation device. The method further comprises repeating steps (b)-(f) for the unprocessed fluid. In these examples, the particulates delaminate from the first fluid flow having a first linear velocity through the first microchannel. The second fluid flow having a second linear velocity through the mesofluidic collection chamber enable sedimentation of the delaminated particles in the high volume mesofluidic collection chamber.

In various embodiments, the mesofluidic collection chamber is primed, may be partially or completely filled with a priming fluid (e.g. buffer solution) prior to the introduction of the unprocessed fluid into the microchannel. In some embodiments, the mesofluidic collection chamber is filled with a priming fluid prior to initiate a flow through the first and/or second microchannels.

Figure 2D:
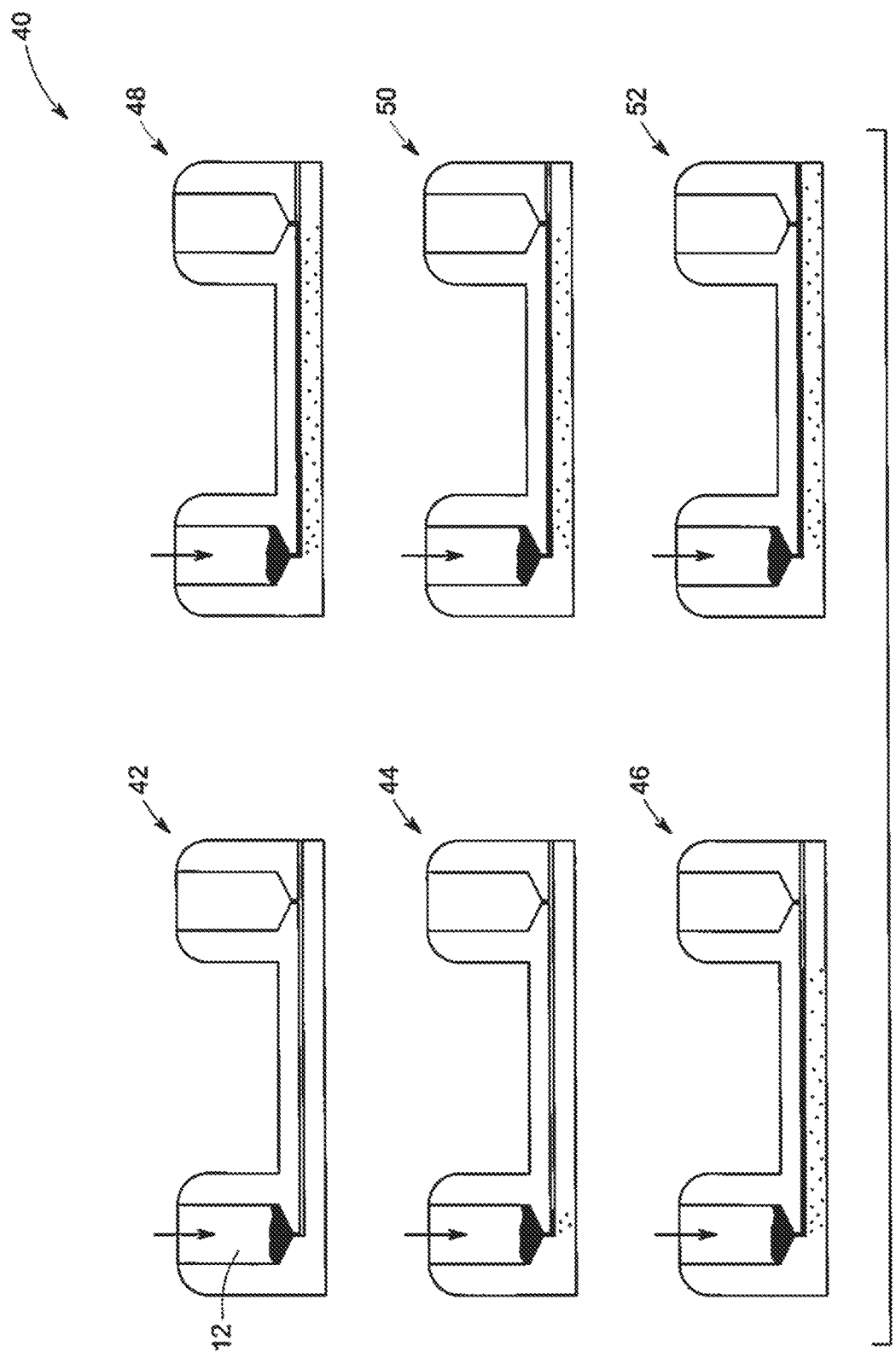
FIG. 2D is a schematic drawing of a perspective view of method steps for separating cells from whole blood using one embodiment of the devices.

Examples of methods for separation of cells from a whole blood sample are illustrated in FIG. 2D. FIG. 2D illustrates separation of cells and plasma from a 0.5 mL sample of whole blood. The method resolves the challenge of using gravity to separate cells in a high throughput manner. As shown in FIG. 2D, the method 40 encompasses various steps of an exemplary embodiment. In step one 42, 0.5 mL sample of whole blood is loaded to the device 10 through the inlet 12. In step two, 44, a vacuum is applied to the outlet 14 of the device to drive the sample through the device. The sample enters to the device from the inlet 12, passing through the microchannel 16 and exits from the device through the outlet 14 (FIG. 2D). In other embodiment of the device, the sample enters to the device from the inlet 12, passing through the first microchannel 17 and exits from the device through the outlet 14A. In some other embodiments of the device, the sample enters to the device from the inlet 12, passing through the first microchannel 17 and exits from the device through the outlet 14 on the second microchannel 19 (not shown). In step three, 46, the device runs until the collection chamber is filled with the captured cells from the whole blood sample. Step four, 48, includes the sedimentation of the cells to the mesofluidic collection chamber and driving out the plasma from the device outlet 14 to a waste chamber or to a second collection chamber. In step five, 50, the cells that entered to the mesofluidic collection chamber 22 due to sedimentation and are visible in the mesofluidic collection chamber from the bottom. In step six, 52, the collection chamber 22 is opened through an outlet to drain the collected cells out form the device 10.

Figure 3:
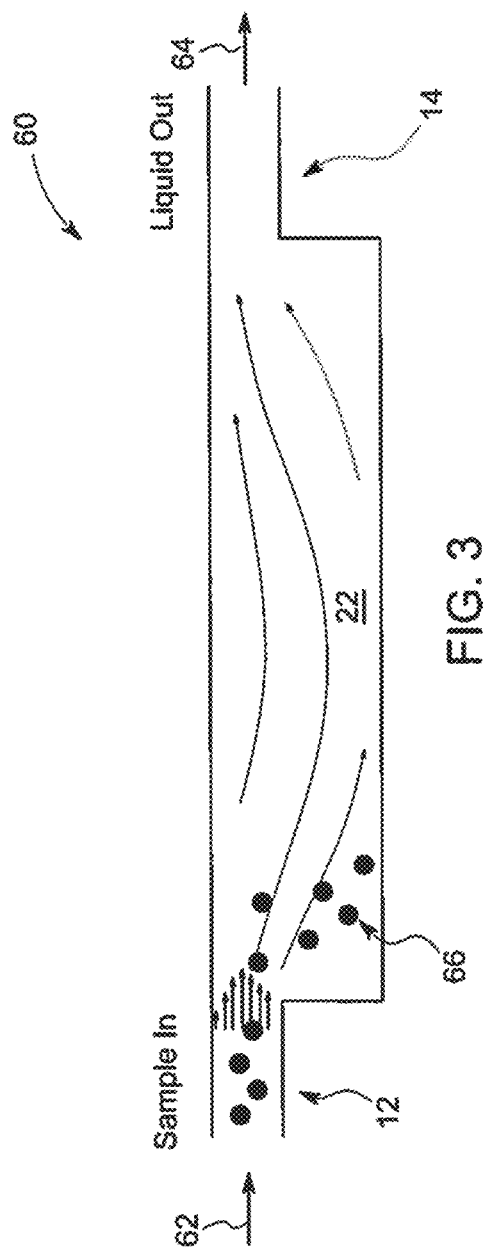
FIG. 3 illustrates a method of separating particulates based on density from a fluid using one embodiment of the devices.

FIG. 3 illustrates one embodiment of a portion of the device 60 under operating condition, wherein the unprocessed fluid (sample) 62 containing particulates 66 enters the device through the device inlet 12 and the processed fluid stream 64 exits the device through the device outlet 14. The particulates 66 are sedimented and trapped into the mesofluidic collection chamber 22. In this embodiment, the percentage of the particulates 66 is significantly reduced in the processed fluid 64, as the particulates 66 are sedimented and trapped within the collection chamber 22.

Figure 4:
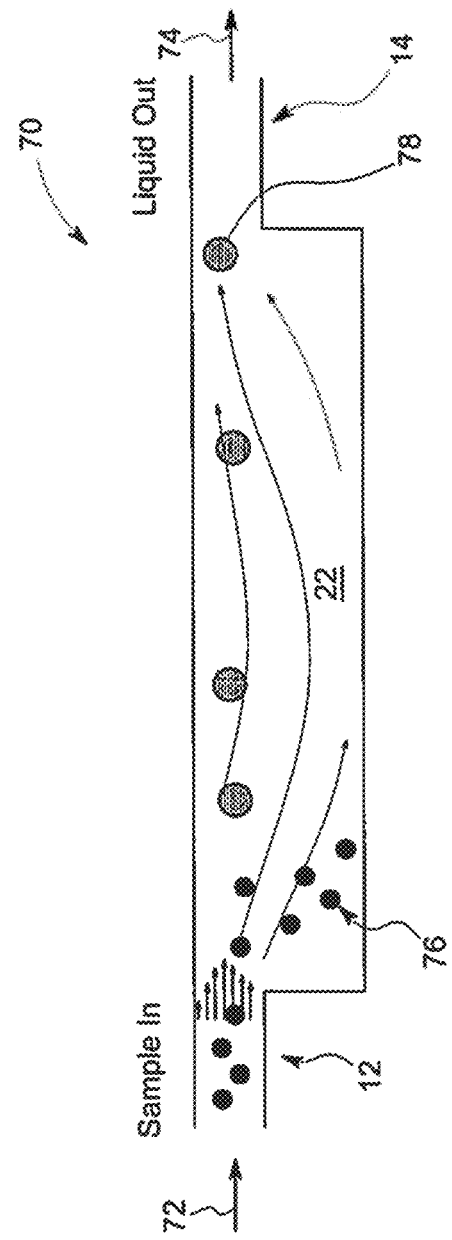
FIG. 4 illustrates a method of separating particulates based on density from a fluid using another embodiment of the devices.

FIG. 4 illustrates an embodiment of the device 70 under operating condition, wherein the unprocessed fluid (sample) 72 comprises particulates of at least two sizes, smaller particulates 76 and larger particulates 78. The sample 72 enters into the device through the inlet 12 and the processed fluid 74 exits from the device through the outlet 14. The larger particulates 78 are not sedimented and trapped into the mesofluidic collection chamber 22, hence particulates 78 are retained within the top portion of the mesofluidic collection chamber and exits out with the processed fluid 74. In this embodiment, the smaller particulates 76 are sedimented and collected to the mesofluidic collection chamber 22, and are separated from the larger particulates 78. In this device, the particulates enter into the mesofluidic collection chamber 22 through sedimentation, unlike a tangential flow filtration process. The differential sedimentation rate of the particulates 76 and 78 results in separation of the particulates using the present device.

FIG. 5 shows another embodiment of the device 80 under operating condition. In this embodiment, the unprocessed fluid (loaded sample) 82 comprises a plurality of particulates 86 and 88, wherein the particulates 86 and 88 have different sedimentation rates. The particulates 86 and 88 are captured in segmented portions 22A and 22B respectively, of the mesofluidic collection chamber. In this embodiment, the similar or same size particulates may be separately sediment in two different segments of the mesofluidic collection chambers 22A and 22B based on the respective sedimentation rate of the particulates. The particulates 86 having higher sedimentation rate sediment faster and are collected in the segment 22A of the mesofluidic collection chamber closer to the fluid inlet. The particulates 88 having lower sedimentation rate sediment later and are collected in the segment 22B of the mesofluidic collection chamber closer to the outlet. The processed sample 84 is driven out from the device outlet.

Another embodiment of the device 90 is shown in FIG. 6, wherein a fluid sample 92 is loaded in the device and a processed fluid 94 is recovered from the fluid outlet. In this embodiment, an additional force, such as a magnetic force field 98 is applied to sediment the particulates 96 and are trapped into the collection chamber 22. The magnetic field is applied across the height ($h_3$) of the mesofluidic collection chamber to allow only certain particulate types to sediment to the mesofluidic collection chamber 22. For example, the particulates 96 having a magnetic property are sedimented to the mesofluidic collection chamber. A population of cells having magnetic property may also be separated from a fluid base using this embodiment of the device.

FIG. 7A is an image from a computational fluid dynamic (CFD) model showing fluid flow pattern through a representative device without a microporous surface. The representative device comprises a first microchannel 17 with one inlet, a second microchannel 19 with a second fluid outlet, and a mesofluidic collection chamber without any microporous surface on it. The representative device without a microporous surface has the same dimension of inlet, outlet, channel length, channel height as of the present device. A significant portion of the fluid flows through the device enters into the mesofluidic collection chamber 22 through the first microchannel 17 and fluid exits through the second microchannel 19. The Comsol® simulation particle trajectories shown in FIGS. 7A and 7B, which demonstrates how the first microchannel 17 entrance to the mesofluidic collection chamber 22 acts to increase cell capture efficiency in the simple device. Particles, which have reached the bottom lamellar flow lines prior to entrance into the mesofluidic collection chamber have a higher probability of interacting with the bottom of the mesofluidic collection chamber and being captured.

Figure 8A:
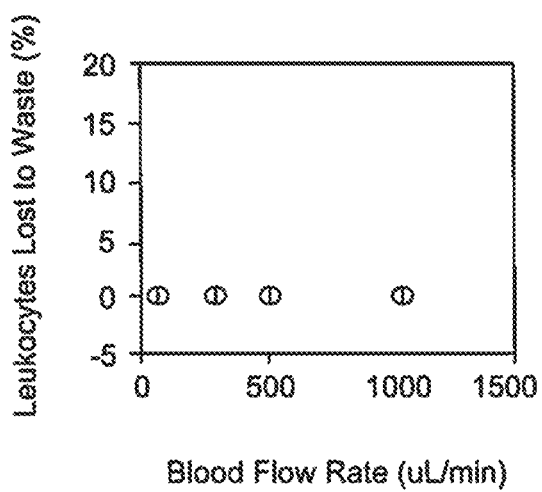
FIG. 8A illustrates performance characteristics of a cell separation device showing loss of leukocytes with increasing fluid flow rate using the device having a microporous body.
Figure 8B:
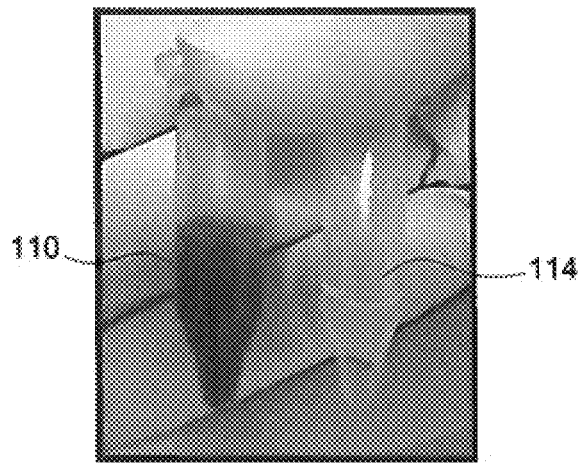
FIG. 8B illustrates performance characteristics of a cell separation device, showing blood sample loaded through inlet and processed fluid samples driven out from the outlet of a device having a microporous surface, respectively.

The capture efficiency of one embodiment the device comprising a microporous membrane is depicted in FIGS. 8A and 8B. A minimum loss of leukocytes observed in the fluid that recovered from the device outlet with increasing fluid flow rate, wherein nearly 100% of the leukocytes of the blood are captured in the mesofluidic collection chamber, as shown in FIG. 8A. A blood sample 110 loaded through a device inlet at a flow rate of 1000 µl/min and a fluid sample 114 recovered from the device outlet using a device, wherein the recovered fluid 114 is clear plasma, which is shown in FIG. 8B.

FIG. 8C illustrates a comparative analysis of qPCR results generated using DNA extracted from equivalent volumes of cells separated using the present separation device and harvested using the standard centrifugation. FIG. 8D shows a diffuse band of low molecular weight DNA captured from the plasma collected to the output chamber (the majority of this DNA are below 500 bp as expected, which is cell-free or circulating nucleic acids in plasma) by separating whole blood sample. FIG. 8D also shows a high molecular weight gDNA band (lane 2), which demonstrates some trace contamination of the plasma sample.

Figure 9:
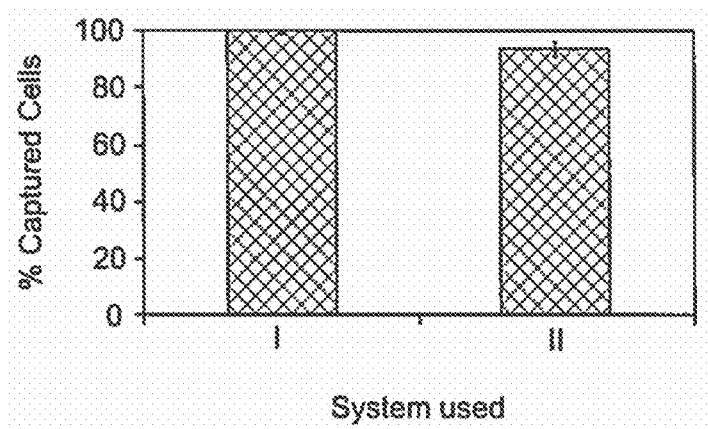
FIG. 9 illustrates performance characteristics of a cell separation device showing a percentage of cells captured in a collection chamber from a blood sample loaded into one embodiment of the device (I) compared with a commercial benchmark (II).
Figure 10:
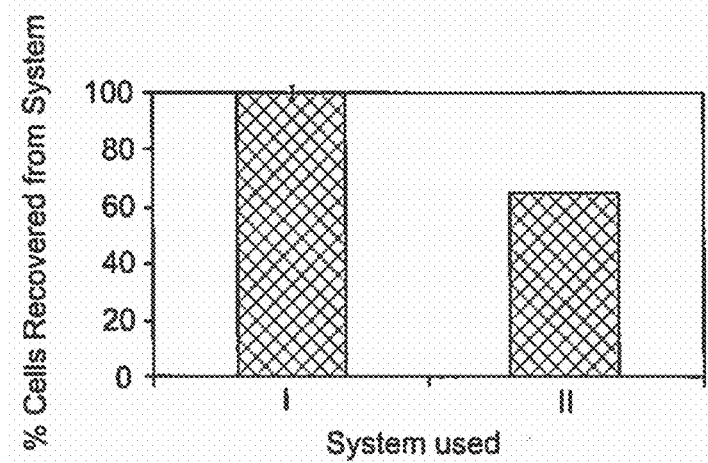
FIG. 10 illustrates performance characteristics of a cell separation device showing percentage recovery of captured cells in accordance with one embodiment of the device (I) relative to a commercial depth filtration (II).

FIG. 9 shows higher cell separation efficiency of the separation device for capturing white blood cells in the mesofluidic collection chamber (I) compared to the cell separation efficiency using a commercial filtration device designed specifically for capturing white blood cells (II). The cell separation efficiency is measured in terms of capture of the white blood cells in the mesofluidic collection chamber. In addition, a common problem with currently available white blood cell filters is loss of cells due to retention within the filter membrane. In contrast, in embodiment of the present device, the loss of cells is addressed by collection of cells within the liquid filled mesofluidic collection chamber below the microporous surface. FIG. 9 shows the ability of the device that competes with traditional filtration techniques for capturing cells. FIG. 10 shows much higher (80%) actual white blood cells recovery (i.e. capture of cells in the mesofluidic collection chamber and then transfer into a standard centrifuge tube for processing) from the present microfluidic device (I) compared to a commercially available cell filter membrane (II) (60%).

Figure 11A:
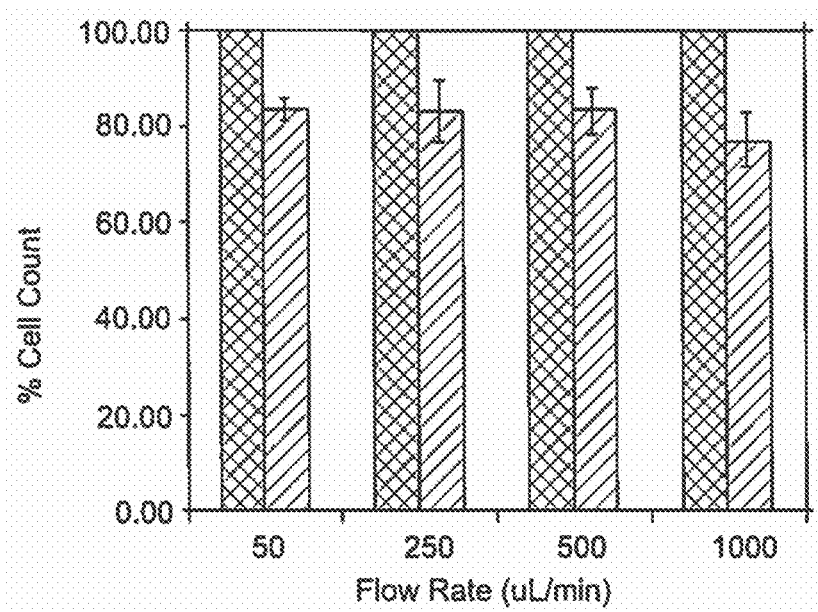
FIG. 11A illustrates performance characteristics of a cell separation device showing a percentage of captured and recovered cells from a blood sample with different flow rates, in accordance with one embodiment of the device.
Figure 11B:
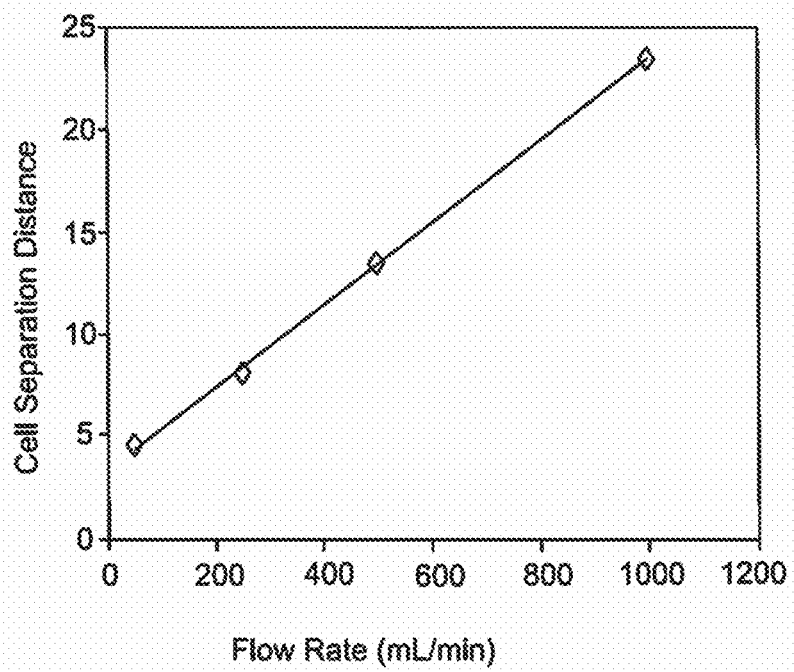
FIG. 11B illustrates performance characteristics of a cell separation device showing length for varying flow rate, in accordance with one embodiment of the device.

FIGS. 11A and 11B are graphical representations of comparative studies between the devices of the present application and commercially available microfluidic separation devices. As illustrated, advantageously, the devices of the present application are configured to allow higher flow rates as compared to flow rates used in the commercially available microfluidic separation devices. Hence, the devices of the present application are more time efficient. The recovery of white blood cells from the processed fluid was consistent for the flow rate range of 50 µl/min to 1 mL/min. The recovery of cells was not decreased at higher flow rates of about 1 mL/min (FIG. 11A). In the present embodiment of the device, the cells sediment and separate from the fluid flow stream after a certain length of the first microchannel. With increase in the flow rate, the length of the first microchannel that is necessary to achieve separation of the cells is also increased, as shown in FIG. 11B. In a non-limiting example, the separation distance is estimated by visual observation of red cell within the device during operation.

Figure 11C:
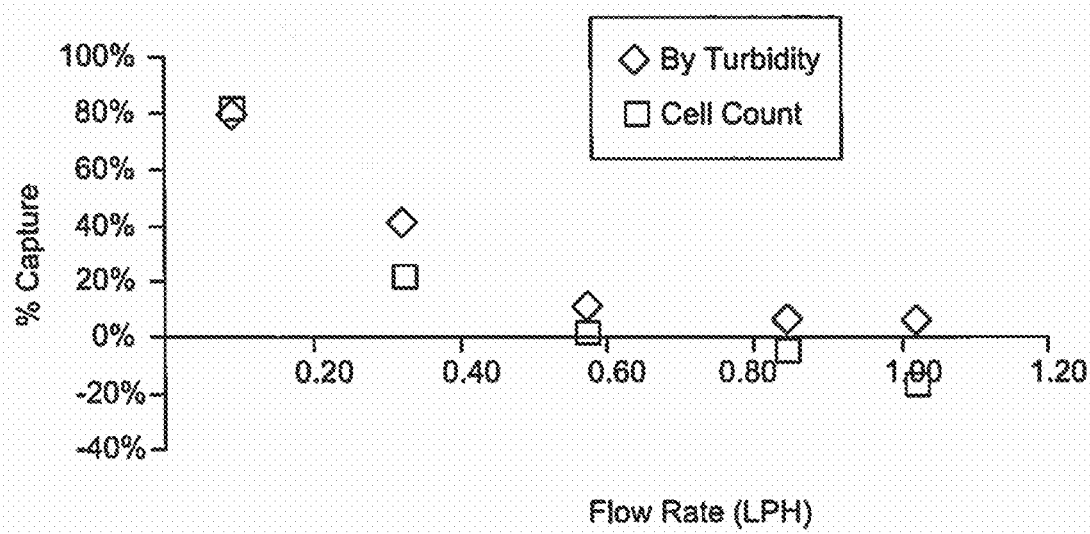
FIG. 11C illustrates performance characteristics of a cell separation device showing a percentage capture of CHO cells with different flow rates, in accordance with one embodiment of the device.

The present device may be used as a cell clarification device for different types of cells, such as CHO or HUVEC. FIG. 11C shows the capture efficiency of the CHO cells using the present device. The separation device is operational with higher flow rates compared to a flow rate used by commercially available microfluidic separation devices. This separation device is beneficial as it enables a non-fouling cell clarification method, which is used for debulking of cells from the bioprocess fluids. Cell clarification is a method of removing cells from a media containing biological products generated by cultured cells. Cell clarification is currently a major burden in the bioprocess industry. Large amount of resources (time, material cost) are expended in multi-step processes, such as in depth filtration and tangential flow filtration. The present device enables a dramatic reduction in required resources by enabling an efficient debulking in a single use, disposable device prior to subsequent purification of the cell product, such as protein.

Figure 11D:
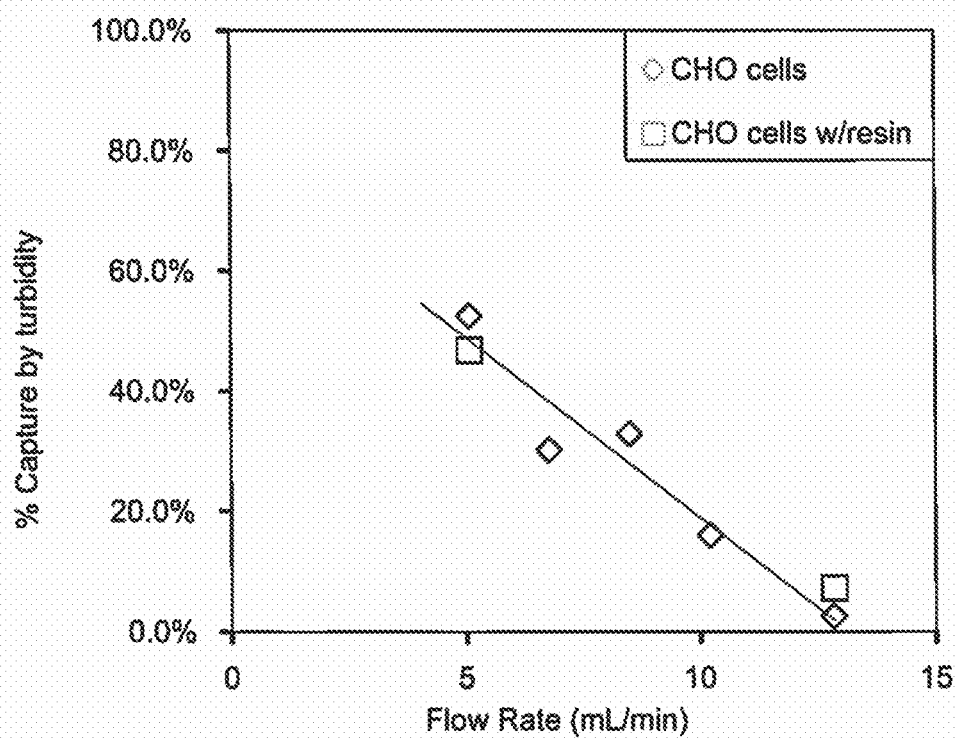
FIG. 11D illustrates performance characteristics of the device in separating resin-bound immunoglobulin G (IgG) from CHO cells at two different flow rates, wherein the resin, immunoglobulin G (IgG), and CHO-cells are present in a cell culture suspension, in accordance with one embodiment of the device.

FIG. 11D shows capture efficiency of the protein-bound resin from a suspension of protein, CHO cells and resin in complete growth culture medium using the present device. In this example, immunoglobulin G (referred to as "protein") was used as a target protein for capture on resin. The cell culture medium-protein-resin mixture was loaded into the separation device as an unprocessed fluid sample. The turbidity was measured for the unprocessed fluid sample (cell culture medium-protein-resin mixture) before loading to the device and after collecting a processed fluid (cells and growth medium) at the output chamber as waste after sedimentation. The resin sedimented faster than the cells and was captured to the mesofluidic collection chamber. It was determined that greater than 90% of cells were purged to the output chamber as a waste at the faster flow rate of 0.77 LPH. The captured particles collected from the device were composed primarily of resin beads bound to IgG. The total IgG concentration captured on the resin was determined to be approximately 63% and demonstrates column-free protein capture using a continuous separation process. This method eliminates the need for traditional chromatography processes including the use of industrial scale columns which are prone to inherit problems such as high pressure drops. By adding resin beads directly into the bioreactor (i.e. a body feed) or into the fluid path of cell culture medium prior to entry into device, resin could bind to desired protein. This mixture may be passed directly through the present separation device to capture resin-bound protein in a continuous manner, without the traditional process steps of cell clarification/debulking (prior to traditional column chromatography).

Figure 11E:
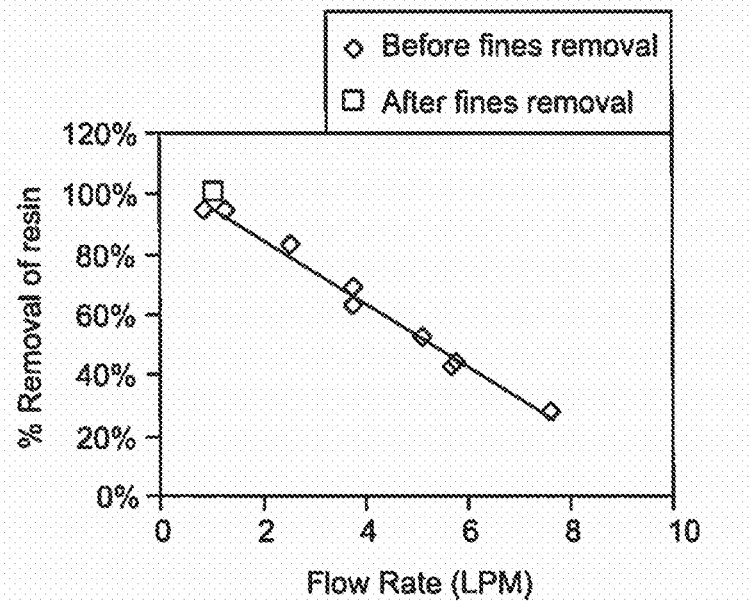
FIG. 11E illustrates performance characteristics of a separation device showing a percentage capture of Sepharose resin from water with different flow rates, in accordance with one embodiment of the device.
Figure 11F:
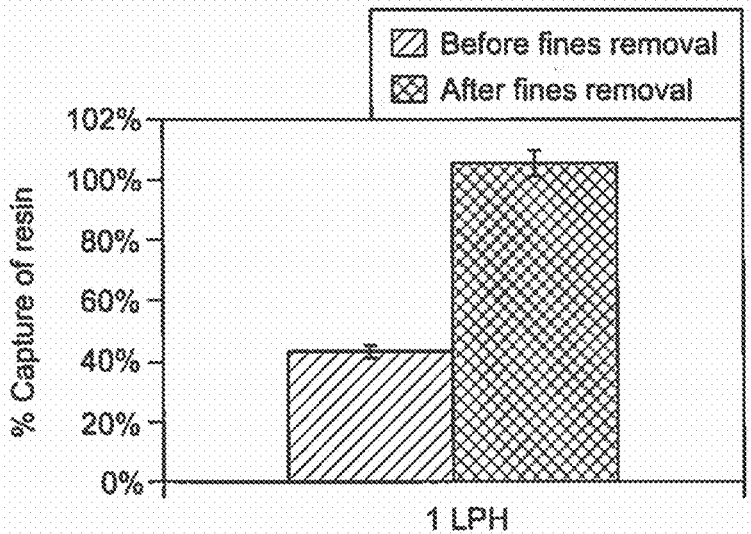
FIG. 11F illustrates performance characteristics of a separation device showing a percentage capture of Sepharose resin from water before and after the elimination of chromatography "fines" at a specific flow rate, in accordance with one embodiment of the device.

FIG. 11E shows the capture efficiency for resin by removing undesirable fine particles from a resin suspension using the present device. The graphs of FIG. 11E and FIG. 11F illustrate the removal efficiency of fine resin particles from a desired Sepharose 4B resin suspension is about 100%.

In one embodiment of the device, additional capture weirs were added to the bottom of the mesofluidic collection chamber. During processing, the weirs act to further limit particles or cells rolling along the bottom of the collection chamber, further delaying the time required for settled particles (versus colloids or liquid) to exit the collection chamber. In one example embodiment, the red blood cells are captured in the weirs within the mesofluidic collection chamber, and clear plasma was collected at the output chamber. In this experiment, 0.1 mL of blood was collected, while 2 mL of washing fluid was run through the device, enabling increased collection efficiencies of plasma contents (such as cell-free nucleic acids).

As noted, the unprocessed fluid sample loaded in the device is a fluidic sample. In some embodiments, the unprocessed fluid sample may include a biological sample, water sample, aqueous slurry, oil slurry, or oil-water emulsion. As noted, the biological materials used in the embodiments may comprise a physiological body fluid, a pathological body fluid, a cell extract, a tissue sample, a cell suspension, a forensic sample and combinations thereof. In some embodiments, the biological material is a physiological body fluid or a pathological body fluid, such as the fluid generated from secretions, excretions, exudates, and transudates, or cell suspensions such as, blood, lymph, synovial fluid, semen, saliva containing buccal swab or sputum, skin scrapings or hair root cells, cell extracts or cell suspensions of humans or animals. In some embodiments, the physiological/pathological liquids or cell suspensions may be extracted from plants. In one or more embodiments, the extracts or suspensions of parasites, bacteria, fungi, plasmids, or viruses, human or animal body tissues such as bone, liver or kidney. In some embodiments, the unprocessed fluid sample is a biological sample selected from whole blood, cell extract, tissue extract or combinations thereof. In one embodiment, the unprocessed fluid sample is whole blood. In some other embodiments, the unprocessed fluid sample is cells in cell culture media suspension, biomolecules (e.g., protein) produced by the cells, and added resin.

In one or more embodiments, the particulate comprises red blood cells, white blood cells, platelets, biological cells, tissue fragments, biomolecules (e.g., proteins), resins, metals, minerals, polymers or combinations thereof.

In some embodiments, the device 8 (FIGS. 1A, 1B, 1C) or 10 (FIG. 2A, 2B, or 2C) may be a portable or field-able device, so that the biological materials can be collected at any location and loaded into the device for cell separation. In some examples, the device may run using a pump. In one embodiment, the device is packaged with a power source, wherein the entire assembly may be self-contained. In such embodiments, the device is portable, simple, and user friendly compared to existing devices in the market.

In one or more embodiments, the device 8 (FIGS. 1A, 1B, 1C) or 10 (FIG. 2A, 2B, or 2C) is at least partially automated. In one or more embodiments, the device 8 (FIGS. 1A, 1B, 1C) or 10 (FIG. 2A, 2B, or 2C) is fully automated. The automation of the device is required to reduce human intervention during collection of cells. The use of an automated device further helps in minimizing contamination during purification of biological samples, aqueous samples, and oil samples. Fully automatic devices are desirable for various applications, wherein the objective is to purify blood cells, blood serum or water or oil from a sample. An externally located controller may be operationally coupled to the device to drive the device, excluding any manual intervention after application of the biological sample, water or oil to the device-inlet.

In some embodiments, the separation device is configured to integrate with another additional device or system, more specifically with an analytical device. As noted, the separation device may have one or more coupling means through which the separation device may integrate with another device depending on the requirement. The coupling means may include but is not limited to, an adapter, or a connector. In some embodiments, the separation device itself is configured to have one or more holders, connecting ports or combination thereof, which may be used to mechanically couple the separation device to another additional device. The separation device may be electronically or mechanically coupled to another additional device for downstream applications.

A schematic representation of the system for separation of particulates is depicted in FIG. 15. The system comprises (a) an input chamber and an output chamber; and (b) a device for separating particulates dispersed within a base fluid and having a relative density difference compared to the base fluid as described above. The device comprises a first microchannel comprising a fluid inlet, a second microchannel comprising a second fluid outlet, and a mesofluidic collection chamber as described above. The input chamber is operatively coupled to the first microchannel via the fluid inlet, and the output chamber is operatively coupled to the second microchannel via the second fluid outlet.

As illustrated in FIG. 15, the system (front view) 51 comprises a fluid inlet 12, a second fluid outlet 14 and a first microchannel 17. The fluid inlet 12 is connected to the mesofluidic collection chamber 22 via a first microchannel 17. The fluid inlet 12 may at times function as and be referred to as an inlet well, which connects to the first microchannel 17. In the embodiment shown, second fluid outlet 14 is connected to the mesofluidic collection chamber 22 via a second microchannel 19. In some embodiments, the mesofluidic collection chamber has an angle of collection 21, such as $\alpha_1$, between the first wall 23 and the bottom wall 25 of the mesofluidic collection chamber. In some embodiments, an angle 29 between the second wall 27 and the bottom wall 25 may be $\alpha_2$. The system further comprises a first fluid driver configured to facilitate flow of the base fluid having the particulates through the first microchannel and to extract at least a portion of a processed fluid from the second microchannel, wherein the processed fluid is enriched in the base fluid and depleted in the particulates.

FIG. 15 further illustrates a system in which a particle removal port, referred to herein as "collection-outlet" 24 is added to the collection chamber to prevent particle build up and filling of the chamber to improve sedimentation (e.g. cell clarification) efficiency. In some embodiments, the system further comprises a second fluid driver 41 configured to recover at least a portion of particulates collected in the mesofluidic collection chamber. In these embodiments, second fluid driver 41 may be coupled to the one or more collection-outlets. For continuous sedimentation and separation process, the collection outlet continuously drains out the collected particles dispersed in a fluid. The particles dispersed in that fluid is collected outside of the system by using a fluid driver, such as a pump 41.

The system comprises a controller unit 43 (FIG. 15) comprising one or more controllers for controlling one or more of the force field, a first linear velocity of a fluid flow through the first microchannel, a second linear velocity of a fluid flow through the second microchannel, and a third linear velocity of a fluid flow through the mesofluidic collection chamber. An externally located controller may be operationally coupled to the system to drive the system, excluding any manual intervention after application of the biological sample, water or oil to the device-inlet.

The system may further include a sensor unit 45 (FIG. 15) comprising one or more sensors, such as temperature sensor, pressure sensor, flow sensor or pH sensor, depending on the requirement and to allow real time monitoring of the system.

In some embodiments of the system, the input chamber 35 is configured such that the particulates dispersed in the base fluid traverse through the first microchannel in a batch process. In the system, 37 is the output chamber. In these embodiments, the collected particulates in the mesofluidic collection chamber are drive out in every batch through one or more of the collection-outlets using a fluid driver 31, such as a pump. In some other embodiments of the system, the input chamber is configured such that the particulates dispersed in the base fluid traverse through the first microchannel in a continuous process. In these embodiments, a collection-outlet may be coupled to the mesofluidic collection chamber, through which the collected particulates, such as cells may be recovered in a continuous manner. In these embodiments of the continuous process, the system is used for debulking in bioprocess applications. For example, when the system has a bioreactor as the input chamber, the cultured cells in the medium are passed through the separation device for debulking of cells from the cell culture medium in a continuous separation process. The system can be used for applications for continuous processes, such as in perfusion regimes in bioprocessing. The addition of a particle removal port (e.g. on the bottom of mesofluidic collection chamber) allows continual flow into the input chamber to microchannel to the mesofluidic collection chamber while simultaneously removing the captured particles. This would eliminate the need for purging (e.g. reverse flow) at the time of maximal particle collection in the mesofluidic collection chamber. The system is significantly scalable from the high volume/flow rates as described above for bioprocess applications to blood processing applications, however it may also be used in low volume/flow rates for use with rare cells collection and isolation.

In certain configurations of the system, the system may comprise more than one device. As such, in certain embodiments, one or more devices may be used in series or in a parallel configuration to increase output.

In one or more embodiments, the system further comprises one or more containers as output chambers 37 for collecting waste or fluid after separation of the particulates or cells. In embodiments, where blood is a sample, the plasma generated after separation of the cells may be collected to a waste chamber. In some other embodiments, when the sample is water or oil, after separation of the particulates, the purified fluid may be collected to a collection chamber coupled to the second fluid outlet. This output chamber is different than the mesofluidic collection chamber. In one or more embodiments, the non-limiting examples of output chambers may be a bag, chamber or other vessels sized based on fluid flow. The output chambers may be disposable or reusable. In certain embodiments, various components of the system may be operationally connected to each other using conduits, holder, adapter, or valves.

In some embodiments of the system, one or more of the input chamber 37, the fluid inlet, the second fluid outlet, the first microchannel, the second microchannel, the mesofluidic collection chamber, and the output chamber is configured to operatively couple to an analytical device. In one or more embodiments, the system as shown in FIG. 15 is at least partially automated. In one or more embodiments, the system is fully automated. The system comprises a processor unit 39 for automatically driving the system (FIG. 15). The automation of the system may reduce human intervention during continuous separation process, batch wise separation process or for differential separation of particulates. The use of an automated system may further assist in minimizing contamination during purification of biological samples, aqueous samples, and oil samples.

The applications for the device or system include, but are not limited to, therapeutic application, biochemical analysis, proteomics, healthcare related applications, pharmaceutical or biotech research applications, in vitro diagnostic and point-of-care applications, medical devices or environmental monitoring including but not limited to water or petroleum applications.

EXPERIMENTAL

Device Fabrication

The separation device as shown in FIG. 1A-2C was fabricated through adhesive lamination of rapid prototyped components. The input chamber was designed to hold up to 1 mL input volumes of whole blood, while the plasma collection chamber was designed with 1.5 mL capacity to eliminate the potential for overfilling. The millimeter scale mesofluidic collection chamber was connected to the input and collection chambers through two microchannels, such as first microchannel and second microchannel, and covered with a microporous membrane (medical grade polyamide mesh, 40 µm woven pores). The plasma chamber was sealed with metal foil, such that whole blood loaded into the input chamber could be drawn through the entire device by applying a vacuum to the collection chamber. The device was first primed with an isotonic buffer to maintain integrity of the captured blood cells during plasma collection; as a result, the final concentration of plasma collected was diluted by the volume of buffer required to prime the device.

FIG. 2D shows the loading of 0.5 mL of whole blood into the device and blood cell capture in the sedimentation chamber. FIG. 8D is an image of the liquid fractions collected from the mesofluidic collection chamber (cell containing fraction) and plasma collected to the output chamber. Blood cell quantification before and after plasma collection was performed using a Sysmex blood analyzer. During testing, an airtight syringe was attached to the vacuum port on the plasma collection chamber, and blood was drawn through the device at controlled speeds using a syringe pump. Efficient blood separation was also accomplished using a simple, uncontrolled, hand-actuated syringe demonstrating high flexibility in device operation parameters.

Figure 13:
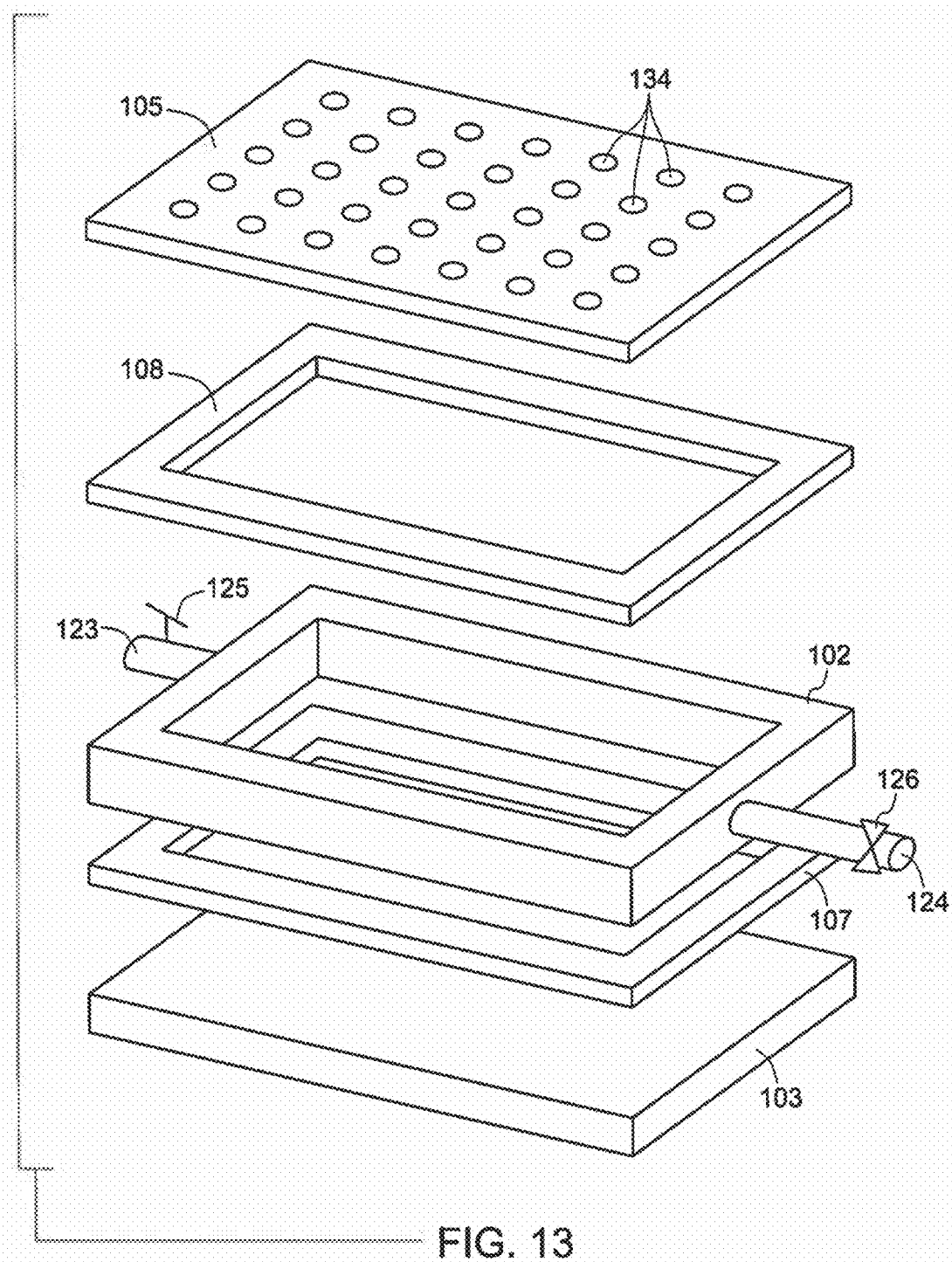
FIG. 13 illustrates an embodiment of a portion of the separation device of FIG. 12 in an exploded perspective view.
Figure 14:
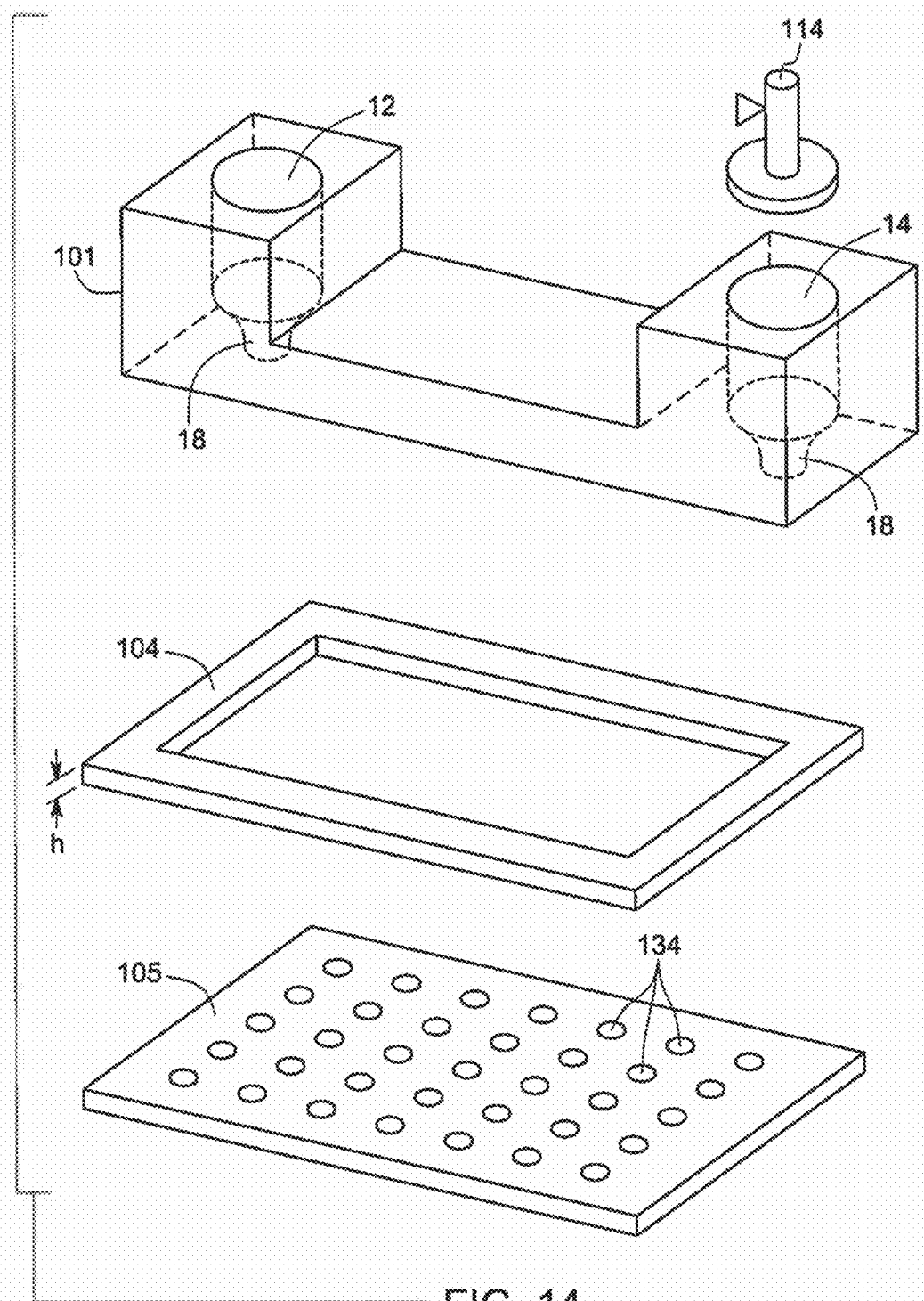
FIG. 14 illustrates an embodiment of a portion of the separation device of FIG. 12 in an exploded perspective view.

A microfluidic separation device housing was created using a rapid prototyping instrument and an ABS-like photopolymer (DSM Somos WaterShed XC 11122). The microfluidic separation device was assembled from three parts, created on the rapid prototyping instrument together with a porous KAPTON film which served as the microporous body or microporous surface, and a set of pressure sensitive adhesive films which joined the parts together and served to create the microchannel. The fabrication design is illustrated in in FIGS. 12-14

Figure 12:
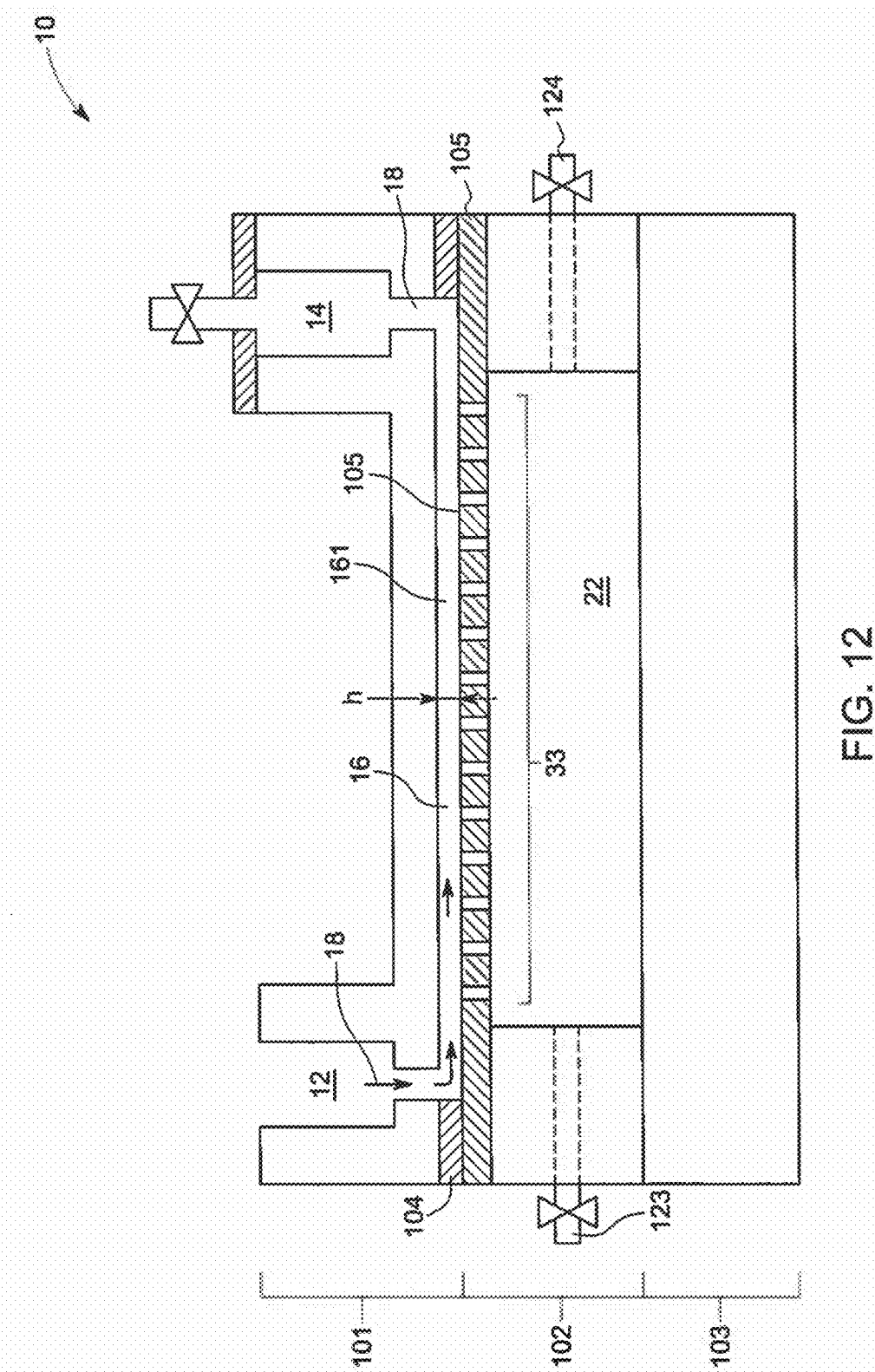
FIG. 12 illustrates a schematic representation of a front view of one embodiment of the separation device.

The first part 101 (FIG. 14) comprised a fluid inlet 12 and second fluid outlet 14 with slots 18 linking each to microchannel 16 (FIG. 12). The second part 102 (FIG. 14) defined the collection chamber 22 (FIG. 12). A third part 103 (FIG. 13) formed a wall of the collection chamber. A 50 micron (µm) thick pressure sensitive adhesive 104 (FIG. 14) was used to define the microchannel having dimensions 50 millimeters by 10 millimeters by 50 microns and comprised features cut out using a cutter/plotter (Graphtec Craft Robo ProS). The adhesive film 104 also served to fix the microporous body 105 (FIGS. 12-14) (the porous KAPTON film) to the first part 101. Additional cut adhesive films 106 and 107 were used to fix the second part 102 to the microporous body 105 and the third part 103 respectively. In the embodiment shown microporous body 105 comprises pores 134.

Two different types of microporous bodies were used in the devices. The first type of microporous body was formed from a KAPTON sheet with laser-machined pore arrays having average pore diameter of about 21.7 microns with a 50 micron center-to-center pore spacing. The second type of microporous body employed was a medical grade polyamide woven mesh having 40 micron pores and 40% porosity (SEFAR MEDIFAB, 07-40/40).

The collection chamber 22 defined by second part 102 had dimensions of 40 millimeters by 10 millimeters by 2 millimeters, resulting in a 750 microliter (µL) holding volume. As configured, the microfluidic separation device could process a total volume of about 0.5 milliliters of blood before the collection chamber reached its maximum cell holding capacity.

Device Operation

The microfluidic separation device was equipped with two ports 123 and 124 (FIGS. 13-14) which enabled the device to be primed easily before use. Typically, the device was primed by introducing deionized water through one of the two ports 123 and 124 and completely filing both the collection chamber 22 and the microchannel 16 before use. Alternatively, the device could be primed by flowing deionized water from the fluid inlet and into the microchannel and collection chamber. Typically, the priming liquid could be introduced into the microfluidic separation device without introducing air bubbles.

Once primed, a sample fluid comprising particulates dispersed with a base fluid (such as whole blood comprising blood cells are the particulates) dispersed within blood plasma (the base fluid) was introduced into fluid inlet 12 and was made to flow through the microchannel 16 contact the upper surface of the microporous body by the application of a vacuum on the second fluid outlet 14 side of the device. Owing to the gravitational forces present, particulates within the unprocessed sample fluid flowing within the first microchannel tended to sediment downwardly into the underlying water-filled mesofluidic collection chamber, wherein the downward motion of the particulates continued. Operation of the separation device typically effected at least a substantial separation of particulates and base fluid. The processed fluid, a mixture of the base fluid and water exchanged with the collection chamber was collected in the second fluid outlet.

EXAMPLES

Cell separation-whole blood or cell-suspensions were used to test collection efficiencies of mammalian cells using the microfluidic separation device. Typical white blood cell dimensions are 10 to 12 microns, and thus the microporous body having 21.7 micron pore diameters provided an about a 2 to 1 ratio of pore diameter to cell dimension. A syringe pump was attached to the second fluid outlet used to create a flow of the cell-containing sample in the fluid inlet through the microchannel and into the second fluid outlet at defined rates (PicoPlus syringe pump, Harvard Apparatus) from 50 to 1000 microliters per minute ($\mu$L/min). Phosphate buffered saline (PBS), deionized water or cell culture medium were used as priming fluids. Separated base fluid was collected by pipetting from the second fluid outlet. Separated cells were recovered from the collection chamber using a syringe. In all cell separation examples disclosed herein, the external force field which caused the cells to traverse the microporous body from the microchannel to the collection chamber was gravity and the microfluidic separation device was oriented such that the passage of cells from the microchannel to the collection chamber was in a downward direction.

Cell collection efficiency was assessed on a Sysmex XE2100 Hematology Analyzer and provided red and white blood cell counts from whole blood samples. White blood cell viability and collection efficiency were assessed on a NucleoCounter® (chemometec) Live/Dead Analyzer. Collection efficiencies were recorded as the ratio of the number of cells introduced through the device fluid inlet 12 (FIG. 12) to the number of cells collected in the mesofluidic collection chamber 22 (FIG. 12). The number of cells actually recovered from the collection chamber was also recorded as there was some additional loss of cells during the transfer of the contents of the collection chamber. Total cell loss was significantly less than losses occurring in standard filtration protocols used for white blood cell capture. Viability of the cells was not affected by passage through the microfluidic separation device over the range of flow rates tested. Cell collection efficiency was assessed at sample flow rates of from 50 microliters per minute to 1000 microliters per minute ($\mu$L/min). In addition, a total surface area of the microporous body necessary to enable efficient cell separation was estimated for each flow rate.

Example 1

Analysis of Cell-Separation Using Computational Fluid Dynamics (CFD)

Computational Fluid Dynamics: A finite element method analysis solution to the full Navier-Stokes equation was also performed using Comsol® multiphysics. Velocity fields were extracted for scaled devices (large enough to model ten pores across the microporous surface) with and without the microporous surface. This allowed visualization of the effect of the microporous surface on flow conditions within the collection chamber. The output boundary condition was set to pressure at 0 Pa, inflow velocities were set to match the 50 uL/min experimental conditions. Collection efficiencies over a range of particulate/fluid density ratios were estimated using the particulate tracing function in Comsol®, and counting the number of particulates that entered the pore array. Additional simulations were then run to investigate the effect of changing the particulate/pore size ratio for densities that match those reported for white blood cells and plasma in the literature. FIGS. 7A and 7B show CFD model analysis of blood sample passing through a representative device without a microporous surface and a device with a microporous surface, respectively.

Whole blood (0.5 mL) was introduced into the fluid inlet of a primed microfluidic separation device and caused to flow through the device at a flow rate of 1000 $\mu$l/min. A microfluidic separation device without a microporous body that separate the collection chamber from a microchannel was used as a control. This device had an idealized configuration and fluid dynamics is shown in FIG. 7A provides a useful point of reference and shows fluid dynamics using an idealized microfluidic separation device with the first microchannel extending fully across the separation area 33. The efficiency of cell separation was strongly dependent of sample flow rate through the device.

A finite element solution to the full Navier-Stokes equation was performed for the device using Comsol® multiphysics software. Velocity fields were extracted for multiple versions of the device with varying dimensions for the mesofluidic collection chamber, the first microchannel entrance to the mesofluidic collection chamber, and for devices with or without the microporous membrane over the mesofluidic collection chamber. The output boundary condition was set to 0 Pa, and inflow was set to 50 or 500 $\mu$L min-1. Particle collection efficiencies were then modelled using the particle tracing function in Comsol, setting the particle/fluid density ratio and size to simulate white blood cells. These modelling results were used to determine final device dimensions (i.e. 2 mm deep sedimentation chamber, 100 $\mu$m input microchannel height, and 25 $\mu$m diameter micropores in the cover) for experimental verification of the cells and particle capture efficiencies (i.e. silica particles or white blood cells from whole blood).

The Comsol® simulation particle trajectories shown in FIG. 7A-7B, which demonstrates how the microchannel entrance to the mesofluidic collection chamber acts to increase cell capture efficiency in the simple device. The three distinct particle paths shown within the sedimentation chamber were generated by "loading" particles at the center line of the upper third, middle third, and bottom third of the microchannel entrance (i.e. the particle was placed in the upper, middle, or lower cross-section of the microchannel entrance). The model shows that there is an expansion of lamellar flow lines from the microchannel into the collection chamber. As a particle passes from the microchannel inlet to the collection chamber, it follows its respective lamellar flow line and the particle distribution is preserved as a function of relative channel height. Sedimentation of cells to lower flow lines within the microchannel acts as a high speed concentrator of cells into the lowest flow lines in the sedimentation chamber and decreases the transit times required to capture particles. Practically, this enables rapid cell stratification in the microchannel while maintaining large volume capacity in the sedimentation chamber, drastically increasing the cell capacity and throughput of the device compared to current microfluidic plasma separators.

Example 2

Recovery of White Blood Cells from Whole Blood Using a Separation Device Having a Microporous Body and a Representative or Control Device without a Microporous Body FIG. 8A illustrates highly efficient blood cell capture at high volumetric flow rates for a prototype separation device having dimensions 25×75 mm. The separation device comprises microchannels and microporous membrane. FIG. 8A demonstrates that the hybrid structure of microchannel, microporous membrane and mesofluidic collection chamber decreases the loss of white blood cells to the output chamber (where plasma is collected). The cell contamination within the output chamber (plasma collection chamber) decreased to <1%.

Whole blood (0.5 mL) was introduced in the fluid inlet of a primed microfluidic separation device and caused to flow through the device at a flow rate of 50, 250, 500 or 1000 μl/min. The separation device is identical to that used in present Example with the exception that no microporous body to separate the mesofluidic collection chamber from a first microchannel was used as a control. FIG. 8A illustrates high cell separation efficiency and minimum loss of cells to the waste with increasing flow rate using the separation device with microporous body. A significant number of leukocytes of the blood were captured and recovered in the mesofluidic collection chamber of the device.

Example 3

Recovery of Red Blood Cells from Whole Blood Using the Separation Device and a Representative Device Red blood cell separation was carried out with a flow rate of 1000 μl/min for a sample consisting of 0.5 mL of whole blood using a primed microfluidic separation device disclosed herein. Separation of the red blood cells from the processed fluid collected in the second fluid outlet was quantitative. Whole blood (0.5 mL) was introduced in the fluid inlet of a primed microfluidic separation device. The plasma recovered from the outlet of the device was observed to be transparent and clear fluid without contamination of the red blood cells, as shown in FIG. 8B. As illustrated in FIG. 8B, element 110 represents an unprocessed blood sample. Element 114 is the processed fluid collected in the second fluid outlet in the presence of the microporous body. FIG. 8B shows the processed fluid 114 as being essentially free of red blood cells.

Example 4

Cell Separation Efficiency Using qPCR Assay

Sysmex Blood cell counter was used for counting cells from whole blood sample. DNA was extracted from equivalent volumes of cells (separated cells, sample 1) that were separated using the present separation device and cells (harvested cells, sample 2) that were harvested using the standard centrifugation. The separated cells (sample 1) and harvested cells (sample 2) were subjected to qPCR analysis. The PCR primers were used against a 380 bp amplicon heme target, wherein the forward primer used was CTCACCCT-GAAGTTCTCAGG (SEQ ID NO: 1), and the reverse primer used was GATGAAGTTGGTGGTGAGG) (SEQ ID NO: 2). A comparative analysis of the qPCR data of DNA extracted from sample 1 and sample 2 is represented by curves shown in FIG. 8C.

DNA was extracted from the plasma collected at the output chamber of the separation device from Example 3. A DNA gel electrophoresis was performed using standard protocol. FIG. 8D is an image of DNA gel electrophoresis showing a diffused band of low molecular weight DNA, which was extracted from the plasma collected at the output chamber (the majority of this DNA is below 500 bp, as expected, for cell-free and circulating nucleic acids in the plasma). FIG. 8D also shows a high molecular weight gDNA band (lane 2), which demonstrates some trace contamination of the plasma sample. A low level of contamination could be from a smaller number of cells that escape capture by the mesofluidic collection chamber, but those cells are not quantifiable using the Sysmex analyzer at these low concentrations in the plasma present in the output chamber. The genomic DNA may also be from damaged cells or cell fragments that escape capture within the mesofluidic collection chamber. In some embodiments, the device may contain a clean-up filter placed between the fluid outlet and the output chamber to further purify trace contaminants in the extracted samples.

Example 5

Separation of Blood Cells from a Whole Blood

The capture efficiency of the separation device compared to other separation technologies may be useful in remote or point-of-care settings. The number of white blood cells (WBCs) escaping capture in the separation device was measured. This number of the white blood cells that were not captured by the mesofluidic collection chamber of the separation device was compared with that of a commercially available standard depth filter (designed for capturing WBCs). The percentage of cells captured was determined by comparing the number of WBCs per mL of sample before and after separation (using the Sysmex blood analyzer), and the experiment was performed in triplicate. 0.5 mL blood samples were run through both devices at 250 μL/min. FIG. 9 shows that the mesofluidic collection chamber provides improved results as compared to standard filtration techniques at high flow rates. The capture efficiency of WBC using the commercial filter required the use of 5 stacked filters (one filter only captured 26.2% of the cells). The stacked depth filters showed a 1 mL dead volume, and did not allow easy capture of the cells. In contrast, FIG. 11A shows that capture efficiency in the mesofluidic collection chamber is maintained across a wide range of operating flow rates (50-1000 μL/min; blue bars). In addition, the mesofluidic collection chamber was flushed and the captured cells were collected for further down-stream analysis.

A whole blood sample (0.5 mL) was introduced into the primed microfluidic separation device configured as in FIG. 12 and was made to flow through the microchannel at a flow rate of 250 μl/min. The processed fluid was analyzed and shown to be free of white blood cells (FIG. 9, left column) The results obtained were compared to the performance of a commercial filter designed for capturing white blood cells. FIG. 9 illustrates the effectiveness of the present invention in overcoming a common problem associated with filtration techniques wherein cell separation efficiency is limited by a tendency of the filter to bind cells.

FIG. 10 illustrates that the actual recovery of blood cells from the mesofluidic collection chamber is enhanced relative to the commercial filter. The recovery of cells from the blood sample was about 80% using the separation device of the present application, whereas cell recovery using the benchmark filter was only about 60%.

Additional experiments were carried out at higher and lower flow rates using the microfluidic separation device configured as in FIG. 12. Results are gathered in FIG. 11A, which show that the processed fluid collected from the second fluid outlet is substantially free of blood cells and that a significant percentage of the blood cells are recoverable from the device following processing. Thus, even at a flow rate of 1000 µl/min (FIG. 11A) the efficiency at which white blood cells were removed from the blood plasma was not decreased relative to the results obtained at a 50 µl/min flow rate. A commercial flow filter was unable to fully separate out cells from 0.5 mL of blood, as the filter stalled at 5 PSI running pressure due to occlusion of the filter pores with captured cells (data not shown). The commercial benchmark also required a stack of 5 filters having a 15 mm diameter each (883.5 mm$^2$ area) in order to achieve separation efficiencies comparable to those observed for the microfluidic separation device provided by the present invention. The length of the first microchannel that is necessary to achieve separation of the cells is increased with increasing flow rate of the fluid, as shown in FIG. 11B. The separation distance is estimated by visual observation of red blood cells within the device during operation.

Example 6

Cell Clarification and Debulking

CHO-M cells were grown and tested in Acti Co-P complete growth media. Cell clarification tests were run at room temperature. Initial cell density was 20×10^6 cells/mL with a turbidity of 634 NTU. A 2 L container of cells was agitated by magnetic stir bar and pumped via peristalsis to the inflow port of the device. A flow rate of 90 mL/hour was used in this example to achieve 93% cell capture efficiency with a reduction in turbidity from 630 to 36 NTU of effluent. The estimated mass balance for 35 min pumping at 1.5 mL/min was 52.5M cells moved into mesofluidic collection chamber. After the initial filling of the mesofluidic collection chamber, 14.55 mL of effluent was produced and collected in the output chamber of the device. This effluent contained 0.25× 10^6 cells/mL (3.67 MM cells) or 7% of total cells. A percentage capture of CHO cells with different flow rates using the separation device is determined by measuring turbidity of the unprocessed fluid sample and processed fluid in output chamber and cell count, and graphically represented in FIG. 11C.

This method represents a non-fouling method for debulking bioprocess liquids. Using the present separation device, the volume of media and water for injection (WFI) needed for filter priming may be dramatically reduced if debulking removed the majority of cells prior to secondary purification filtration. Another significant feature demonstrated, is the single use disposable nature of the device. Single use disposable may result in saving a tremendous amount of time and material, as there is no requirement for cleaning, sterilizing and drying the device as required in other standard filtration methods.

Example 7

Extraction of Protein from Cells Cultured in Medium

IgG Capture: Sepharose cross-linked with recombinant protein A (estimated bead diameter of 60-165 m) was purchased from GE-Healthcare. Protein A Sepharose is sold in slurry (50% resin suspended in 20% Ethanol). Assuming that a typical IgG production in cell culture ranges from 10-120 mg/L, a 120 mg sample of bovine IgG was added to 800 mL of cultured cells for a final concentration of 0.15 mg/mL IgG. The cell density of this solution was determined to be 20×10^6 cells/mL. The cells were incubated in the presence of IgG with constant mixing provided by a magnetic stir bar placed in the flask.

A 5 mL recombinant protein A Sepharose taken from the stock solution was centrifuged at 150×g for 10 minutes to remove the ethanol storage solution. The resin was then washed with a 5 mL aliquot of ActiCho P growth media (BioProcess International) and centrifuged for 10 minutes at 150×g. The wash step was repeated 3 additional times after which the 5 mL volume of washed resin was introduced to the cell-protein mixture and allowed to incubate for 10 minutes. After 10 minutes, the cell-protein-resin mixture was pumped via peristalsis to the inflow port of the present separation device at a flow rate of 135 mL/min. The turbidity of the cell-protein-resin mixture was 823 NTU (Nephelometric Turbidity Units). At this flow rate, 97% of the cells were passed to the waste stream. The majority of cells were visible, passed through the mesofluidic collection chamber at the same flow rate of 135 mL/min and moved to the output chamber and collected as a waste, wherein the protein-bound resin was settled and was captured in the mesofluidic collection chamber. The waste of the output chamber had a turbidity of 764 NTU indicating greater than 90% suspended bodies had been purged to the waste. The captured fluid, composed primarily of resin beads, was purged from the device and tested for protein (e.g., IgG) concentration measurement. A low pH elution buffer (1M Tris-HCL: 0.1M Citric Acid, pH 3) was then added to the captured resin and mixed gently for 5 minutes, followed by centrifuged at 150×g. The supernatant was collected and titrated back to pH of 7.4. The protein concentration of the collected IgG was determined by HPLC. By HPLC run, the potential fragmentation and/or aggregation of the protein (IgG) were also determined. FIG. 11D shows capture efficiency of 63.2% for the collected protein bound resin. The resin pellet was saved and washed in 20% ethanol buffer for recovery of the recombinant protein A Sepharose.

This method may eliminate the need for traditional chromatography processes including the use of industrial scale columns. Often, the traditional chromatography columns are difficult to handle and expensive to employ in the production industry, such as resin packing, preparing and filling of media. By using a body feed of resin directly into the bioreactor or in the fluid path prior to entry into the device, the resin may bind to the desired protein produced by the cultured cells and be passed directly through the separation device, without the traditional process steps of cell clarification/debulking. Cost savings may be accomplished in media reduction, column reduction and footprint reduction of required material/equipment.

Example 8

Fine Particles Removal from a Resin Using the Separation Device of the Present Application Twenty milliliters Sepharose 4B resin suspension from Aldrich was added to 300 mL of deionized water in a spinner flask. A pressure was applied to the resin suspension in the flask. The pressurized resin suspension was loaded to the separation device at a rate of 1.3 LPH (liters per hour). The settled resin was captured in the mesofluidic collection chamber of the device and the fine particles were passed through the second microchannel as a waste stream and collected in the output chamber. The turbidity of the feed suspension was 35 NTU and the turbidity of the resulting waste stream was 2.8 NTU indicating that 92% of the resin was captured in the mesofluidic collection chamber of the device. The captured resin stream was reintroduced into the spinner flask and diluted to 300 mL with fresh deionized water. Pressurization of the spinner flask and passage of the suspension through the separation device at a reduced flow of 1 LPH resulted in a waste with turbidity of 0.7 NTU which was equivalent to that of our deionized water, 0.9 NTU, indicating that capture of Sepharose 4B resin was about 100% after removal of undesired fine particles, which is illustrated in FIGS. 11E and 11F.

This process enables a method of efficiently removing undesirable resin particles (i.e. "fines" such as small, misshapen). Current methods for removal of impurities from the resin require multiple steps including packing of column, filling with media and allowing small resin particles to remove prior to column chromatography. On a selective basis, the separation device may be customized to select for (and likewise eliminate) particular size ranges of the particles by taking advantage of the selective sedimentation rates of particles based on density and settling velocity differences. The method may be used to increase yield and purity of the resin products through removal of the "fines" prior to the protein binding stage in production. As such, the protein would not be bound to the undesirable resin particles and lost to waste as the complex (fine resin+protein) passes through the column or the device due to size and settling velocity.

Example 9

Capture Efficiency of Rare Cells

Extension of applications of the device to rare cell capture (with syringe actuation) was investigated. In one example of the versatility of the device, capture of a low number of input cells was tested. In this experiment, pre purified peripheral blood mononuclear cells (PBMCs) was diluted to 18,000 cells/ml (lower concentration) and 250,000 cells/ml input (higher concentration). In addition, the device was run through hand actuation of a syringe. The syringe was connected to the output chamber, where typically plasma is getting collected, in order to generate vacuum for running the device. In the experiment with rare cells, the device enabled capture of 7880/18000 input cells (with 74.8% viability) at the lower concentration and 114,600/250,000 cells (with 97.6% viability) at the higher concentration, even without external equipment (i.e. syringe pump).

While only certain features of the invention have been illustrated and described herein, many modifications and changes will occur to those skilled in the art. It is, therefore, to be understood that the appended embodiments are intended to cover all such modifications and changes as fall within the scope of the invention.

---

The invention claimed is:

1. A separation device for separating particulates dispersed in a base fluid, the device comprising:
   a fluid inlet; a fluid outlet;
   a first microchannel disposed between the fluid inlet and the fluid outlet and having a height $h_1$ in a range of 1 to 1000 microns and a length li; and
   a mesofluidic collection chamber comprising a height $h_3$ in a range of 2 mm to 20 mm and coupled to the first microchannel on a first side of the mesofluidic collection chamber;
   the device configured such that the particulates dispersed in the base fluid traverse through the first microchannel and are caused to migrate through the device by a force field applied across one or more dimensions of the first microchannel, and
   the particulates delaminate from the base fluid, generate lamellar flow lines and are driven into a specific laminate of a plurality of layers of the base fluid flowing within the first microchannel and wherein the particulates follow their respective lamellar flow lines during fluidic expansion from the first microchannel to the mesofluidic collection chamber while entering into the mesofluidic collection chamber, wherein at least a portion of the particulates in at least a portion of the base fluid are collected in the mesofluidic collection chamber.

2. The device of claim 1, further comprising a second microchannel having a second fluid outlet disposed at a second side of the mesofluidic collection chamber, such that the fluid inlet, first microchannel, second microchannel, and second fluid outlet are in a fluidic communication via the mesofluidic collection chamber, and wherein the second microchannel has a length $l_2$ in a range from about 5 millimeters to about 100 millimeters and a height $h_2$.

3. The device of claim 2, further comprising an input chamber operatively coupled to the first microchannel via the fluid inlet.

4. The device of claim 3, further comprising an output chamber operatively coupled to the second microchannel via the second fluid outlet.

5. The device of claim 2, wherein the lengths $l_1$ and $l_2$ are each in a range from about 16 millimeters and about 70 millimeters.

6. The device of claim 1, wherein the force field comprises a gravitational field.

7. The device of claim 1, wherein the force field comprises an applied magnetic field, an applied electric field, an acoustic field, or combinations thereof.

8. The device of claim 1, wherein the mesofluidic collection chamber has a length $l_3$ in a range from about 1 centimeter to about 25 centimeters.

9. The device of claim 1, further comprising a microporous body disposed within the mesofluidic collection chamber.

10. The device of claim 9, wherein the microporous body comprises pores with an average diameter in a range from about 10 microns to about 500 microns.

11. The device of claim 9, wherein the microporous body has a porosity in a range from about 10 percent to about 75 percent.

12. The device of claim 1 further comprising particulate traps positioned in a bottom of the mesofluidic collection chamber.

13. The device of claim 9, wherein the base fluid comprises one or more of a whole blood, cells in culture medium, a cell extract, a tissue extract, a petroleum product, an oil and water emulsion, and water sample and the device separates at least one of a plurality of particulates, cells or biomolecules from the one or more of the whole blood, the cells in culture medium, the cell extract, the tissue extract, the petroleum product, the oil and water emulsion, and the water sample.

14. The device of claim 9, wherein the base fluid comprises a suspended medium and the device selectively separates a plurality of particulates in the suspended medium based on a size of the plurality of particulates.

15. The device of claim 14, wherein the plurality of particulates comprise fine resin particles smaller than a predetermined range of particle size for use in chromatography devices smaller than a predetermined range of particle size.

16. The device of claim 9, wherein the particulates comprise one or more of red blood cells, white blood cells, blood platelets, non-hematic biological cells, tissue fragments, non-cellular biological solid, fine resin particulates, metals, and minerals.

17. The device of claim 16, wherein the particulates comprise one or more of red blood cells, white blood cells, blood platelets, cultured cells, tissue fragments, non-hematic biological cells, or biomolecules.

18. The device of claim 16, wherein the particulates comprise one or more of fine resin particulates, resin beads, metals, minerals.

19. The device of claim 1, wherein the mesofluidic collection chamber further comprises one or more collection-outlets for recovering the portion of the particulates collected in the mesofluidic collection chamber.

20. The device of claim 1, wherein the particulates have a largest dimension in a range from about 1 micron to about 250 microns.

21. The device of claim 1, further comprising one or more controllers for controlling one or more of the force field, a first linear velocity of a fluid flow through the first microchannel, a second linear velocity of a fluid flow through the mesofluidic collection chamber.

22. The device of claim 1, further comprising a first fluid driver configured to:
   facilitate a flow of the base fluid having the particulates through the first microchannel; and
   extract at least a portion of a processed fluid from the device, wherein the processed fluid is enriched in the base fluid and depleted in the particulates.

23. The device of claim 1, further comprising a second fluid driver configured to recover at least a portion of particulates collected in the mesofluidic collection chamber.

24. The device of claim 9, wherein a fluid flow regime of the base fluid comprises a first fluid flow through the first microchannel having a first linear velocity to enable particulate delamination in the first microchannel, a second fluid flow through the mesofluidic collection chamber having a second linear velocity to enable sedimentation of the delaminated particulates in the mesofluidic collection chamber, and wherein the second linear velocity is a fraction of the first linear velocity.

25. The device of claim 1, wherein the device is free of any membrane and porous barrier.

26. A system comprising:
   (a) a separation device for separating particulates dispersed within a base fluid and having a relative density difference compared to the base fluid, comprising:
   a fluid inlet; a fluid outlet;
   a first microchannel disposed between the fluid inlet and the fluid outlet and having a height $h_1$ in a range of 1 to 1000 microns and a length li; and a mesofluidic collection chamber comprising a height $h_3$ in the range of 2 mm to 20 mm and distally coupled to the first microchannel on a first side of the mesofluidic collection chamber;

(b) an input chamber operatively coupled to the first microchannel via the fluid inlet; and (c) an output chamber operatively coupled to the mesofluidic collection chamber via the fluid outlet, the device configured such that the particulates dispersed in the base fluid traverse through the first microchannel and are caused to migrate through the device by a force field applied across one or more dimensions of the first microchannel, and wherein the particulates delaminate from the base fluid, generate lamellar flow lines and are driven into a specific laminate of a plurality of layers of the base fluid flowing within the first microchannel and wherein the particulates follow their respective lamellar flow lines during fluidic expansion from the first microchannel to the mesofluidic collection chamber while entering into the mesofluidic collection chamber, and further wherein at least a portion of the particulates in a portion of the base fluid are collected in the mesofluidic collection chamber.

27. The system of claim 26, wherein the separation device further comprises a second microchannel having a second fluid outlet disposed at a second side of the mesofluidic collection chamber, such that the fluid inlet, first microchannel, second microchannel, and second fluid outlet are in a fluidic communication via the mesofluidic collection chamber, and wherein the second microchannel has length $l_2$ in a range from about 5 millimeters to about 100 millimeters and a height $h_2$.

28. The system of claim 27, further comprising one or more controllers for controlling one or more of the force field, a first linear velocity of a fluid flow through the first microchannel, a second linear velocity of a fluid flow through the second microchannel, and a third linear velocity of a fluid flow through the mesofluidic collection chamber.

29. The system of claim 27, further comprising a first fluid driver configured to facilitate flow of the base fluid having the particulates through the first microchannel and to extract at least a portion of a processed fluid from the second microchannel, wherein the processed fluid is enriched in the base fluid and depleted in the particulates.

30. The system of claim 29, further comprising a second fluid driver configured to recover at least a portion of particulates collected in the mesofluidic collection chamber.

31. The system of claim 27, wherein one or more of the input chamber, the fluid inlet, the second fluid outlet, the first microchannel, the second microchannel, the mesofluidic collection chamber, and the output chamber is configured to be operatively coupled to an analytical device.

32. The system of claim 26, wherein the force field comprises an applied force field selected from among an applied magnetic field and an applied electric field.

33. The system of claim 26, further comprising a microporous body defining at least a portion of the first microchannel, wherein the particulates comprise cells having an average cell diameter (d) in a range from about 1 micron to about 100 microns.

34. The system of claim 26, further comprising a fluid driver, wherein the particulates dispersed in the base fluid traverse through the first microchannel and driven out from the mesofluidic collection chamber by the fluid driver in a batch process.

35. The system of claim 26, further comprising a collection outlet, wherein the particulates dispersed in the base fluid traverse through the first microchannel and recovered from the mesofluidic collection chamber through the collection outlet in a continuous process.

36. The system of claim 35, further comprising a microporous body defining at least a portion of the first microchannel, wherein the base fluid comprises bioprocess liquids and the continuous process is used for debulking of the bioprocess liquids.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcaccctga agttctcagg                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgaagttg gtggtgagg                                               19